(12) United States Patent
Drake et al.

(10) Patent No.: US 11,712,506 B1
(45) Date of Patent: Aug. 1, 2023

(54) FLUID SOURCE MANAGEMENT SYSTEM

(71) Applicant: KYRA MEDICAL, INC., Northborough, MA (US)

(72) Inventors: Jesse Drake, Westborough, MA (US); Mike Nordling, Hopkinton, MA (US); Justin McCarthy, Boxborough, MA (US); Ryan Cunniff, Hopkinton, MA (US); Jeremy MacPherson, Medfield, MA (US)

(73) Assignee: KYRA MEDICAL, INC., Northborough, MA (US)

( * ) Notice: Subject to any disclaimer, the term of this patent is extended or adjusted under 35 U.S.C. 154(b) by 0 days.

(21) Appl. No.: 17/894,842

(22) Filed: Aug. 24, 2022

(51) Int. Cl.
*A61M 1/00* (2006.01)
*A61M 3/02* (2006.01)

(52) U.S. Cl.
CPC .............. *A61M 1/77* (2021.05); *A61M 3/022* (2014.02)

(58) Field of Classification Search
CPC .. A61M 2205/3334; A61M 2205/3344; A61M 2205/502; A61M 3/005; A61M 3/0201; A61M 3/0202; A61M 3/0233; A61M 3/0241; A61M 3/0266; A61M 2039/0027; A61M 39/10; A61M 39/22; A61M 2205/33
See application file for complete search history.

(56) References Cited

U.S. PATENT DOCUMENTS

| | | | | |
|---|---|---|---|---|
| 4,372,304 | A * | 2/1983 | Avakian | A61M 5/16813 251/8 |
| 4,559,036 | A * | 12/1985 | Wunsch | A61M 5/16827 604/247 |
| 4,681,563 | A * | 7/1987 | Deckert | A61M 5/1689 128/DIG. 13 |
| 4,714,463 | A * | 12/1987 | Archibald | A61M 5/16827 604/246 |
| 4,925,444 | A * | 5/1990 | Orkin | A61M 5/16827 604/80 |
| 4,966,579 | A * | 10/1990 | Polaschegg | A61M 5/16827 604/131 |
| 5,429,485 | A * | 7/1995 | Dodge | A61M 5/142 604/152 |
| 5,438,510 | A * | 8/1995 | Bryant | F04B 43/0736 604/67 |
| 6,142,008 | A * | 11/2000 | Cole | A61M 5/365 604/122 |
| 6,695,803 | B1 * | 2/2004 | Robinson | A61M 1/0272 210/252 |
| 7,615,037 | B2 | 11/2009 | Murray et al. | |
| 8,444,592 | B2 | 5/2013 | Williams et al. | |
| 9,511,184 | B2 | 12/2016 | Woolford et al. | |

(Continued)

FOREIGN PATENT DOCUMENTS

EP 3148607 B1 * 7/2019 .......... A61M 1/1656

*Primary Examiner* — Scott J Medway
(74) *Attorney, Agent, or Firm* — Potomac Law Group, PLLC; John J. Penny, Jr.; Reza Mollaaghababa

(57) ABSTRACT

A fluid source management system (100) comprising a structure (101) that supports one or more fluid sources (103), sensors (102) that determine the fluid state of the fluid sources (103), at least one common reservoir (108) for storing the fluid, tubing (104) connecting the fluid sources (103) to the common fluid reservoir (108) and a controller (105) that controls the opening and closing of the tubing (104) based upon the fluid state of the fluid sources (103).

10 Claims, 17 Drawing Sheets

(56) References Cited

U.S. PATENT DOCUMENTS

| | | | |
|---|---|---|---|
| 9,561,323 B2 * | 2/2017 | Plahey | A61M 1/28 |
| 9,707,340 B2 * | 7/2017 | Lee | G16H 20/17 |
| 9,889,246 B2 | 2/2018 | Woolford | |
| 10,064,987 B2 * | 9/2018 | Wright | G16H 20/17 |
| 10,507,319 B2 * | 12/2019 | Haury | A61M 5/1407 |
| 10,518,005 B2 | 12/2019 | Carr et al. | |
| 10,751,451 B2 | 8/2020 | Klein et al. | |
| 11,083,842 B2 * | 8/2021 | Chassot | A61M 5/1407 |
| 11,135,360 B1 * | 10/2021 | Jacobson | G16H 20/17 |
| 11,357,966 B2 * | 6/2022 | Lane | B01F 33/30 |
| 2003/0158508 A1 * | 8/2003 | DiGianfilippo | G16H 40/63 |
| | | | 604/4.01 |
| 2003/0212381 A1 * | 11/2003 | Whitehead, III | A61M 5/16827 |
| | | | 604/514 |
| 2014/0224829 A1 * | 8/2014 | Capone | G05D 7/0635 |
| | | | 222/23 |
| 2016/0101278 A1 * | 4/2016 | Norris | A61M 60/37 |
| | | | 604/29 |
| 2017/0203028 A1 | 7/2017 | Carr et al. | |
| 2019/0262526 A1 * | 8/2019 | Wyeth | A61M 1/1666 |
| 2020/0384169 A1 * | 12/2020 | Planas | A61M 1/0272 |
| 2022/0185538 A1 * | 6/2022 | Wurm | A61J 1/16 |

* cited by examiner

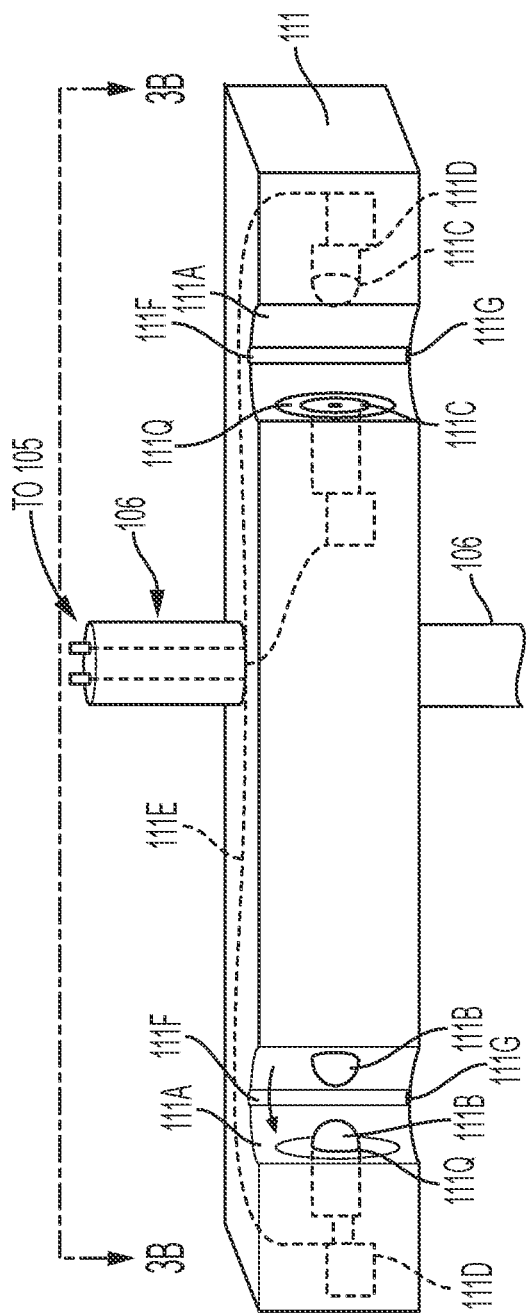
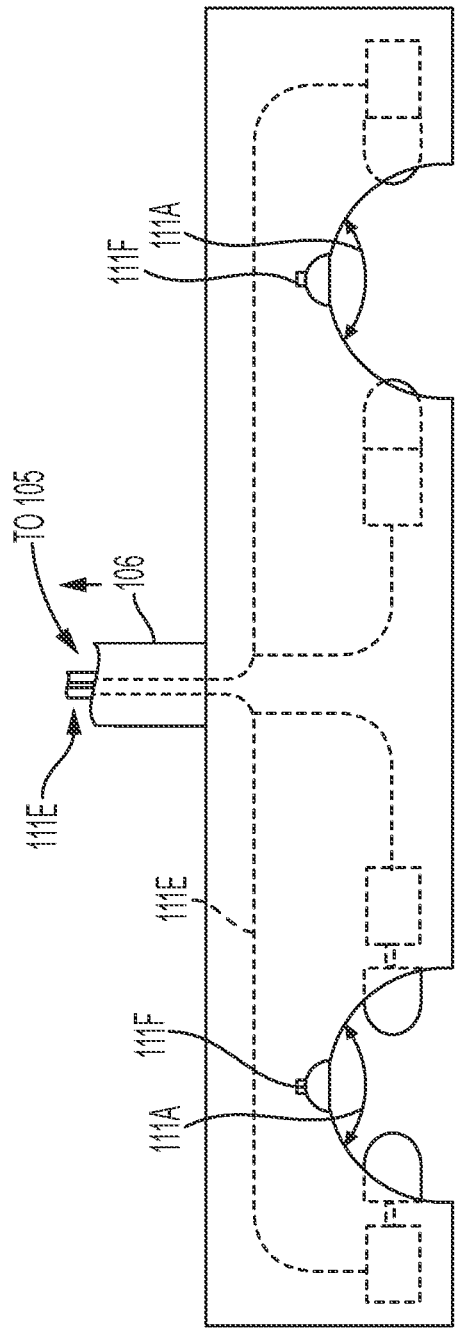

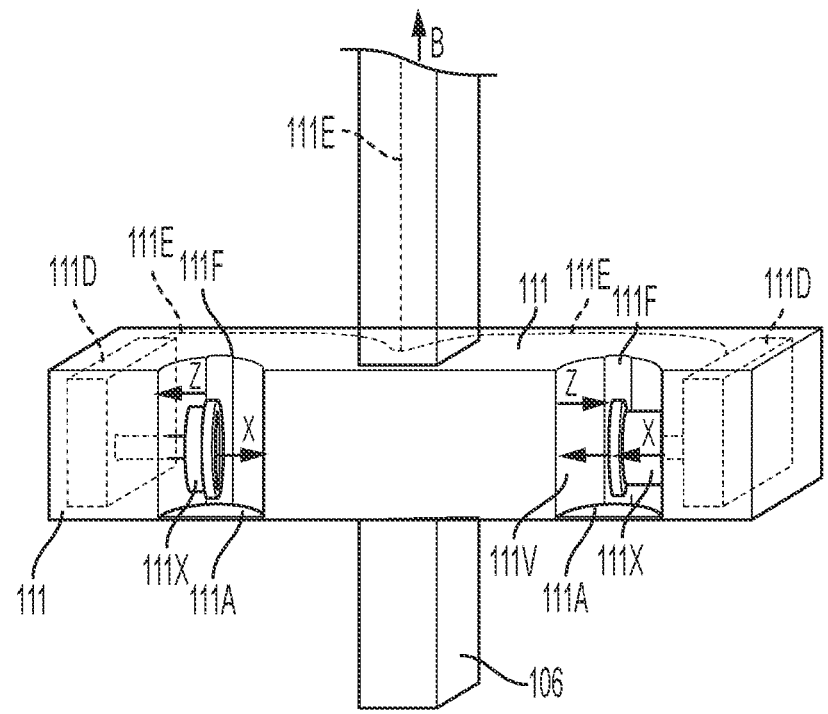
FIG. 12A
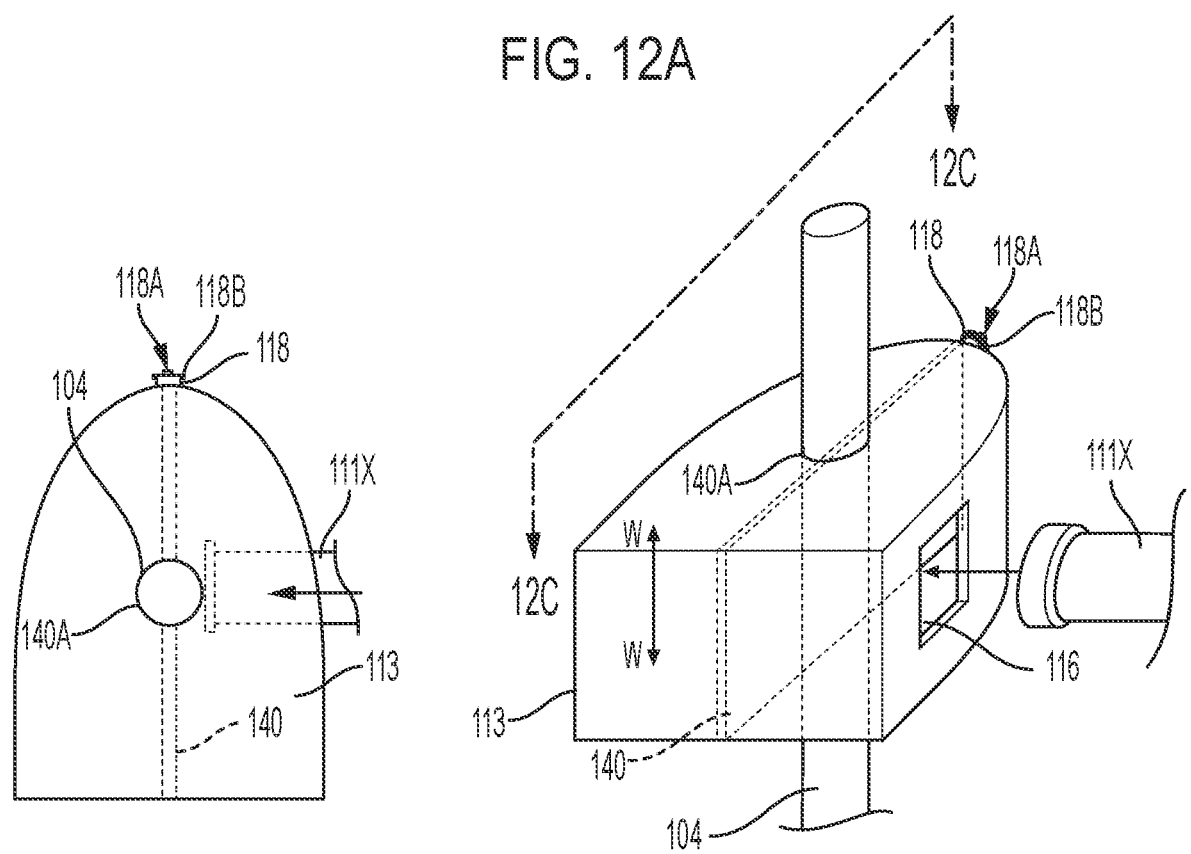
FIG. 12C
FIG. 12B

FLUID SOURCE MANAGEMENT SYSTEM

TECHNICAL FIELD

The present disclosure relates generally to a fluid source management system. More particularly, the present disclosure relates to a fluid source management system for maintaining and supplying surgical fluid during a surgical procedure.

BACKGROUND

In surgical procedures including endoscopic orthopedic cases the clinician may have to cut or remove bone and/or soft tissue. This may be accomplished through the use of surgical instrumentation such as shavers with rotational cutting surfaces which are inserted into the operative joint capsule. Video cameras are placed through trocars inserted through incisions in the joint capsule to allow viewing of the operative site and manipulation of the instrumentation. In order to maintain the needed visual clarity, to remove debris and to expand the operative joint capsule during these endoscopic procedures, a continuous flow of fluid is required. The flow of fluid is maintained by operating room (OR) staff who monitor fluid levels in intravenous fluid bags (I.V bags) which may be directly attached via a tubing set to the instrumentation or to a pump which in turn feeds fluid to the instrumentation and into the joint capsule. This can be done by the clinician hanging an I.V. bag on a pole and attaching a tube or fluid line to the pump. The I.V. bag may feed fluid via gravity flow through the attached tube set into the equipment or into a pump. When a pump is used, it pushes fluid through the tubing and then into the instrumentation and/or the joint capsule. In longer surgical cases, as many as ten to twenty I.V. bags may be consumed. Due to this, the staff may use a Y connector to attach two I.V. bags to the pump in order to minimize the exchange of empty I.V. bags for full ones during the surgical procedure. Sometimes the clinical staff, distracted by other tasks, may allow the I.V. bags to become empty. Modern orthopedic fluid pumps can sense the absence of a fluid supply and may alert the staff with an audible and/or visual alarm in such cases. When this occurs, the staff must cease all other tasks and immediately replace some or all of any empty I.V. bags with full ones in order to maintain or resupply fluid to the pump. If adequate fluid flow is not maintained, the joint capsule may collapse onto the instrumentation and the surgeon may lose visualization as debris is no longer cleared by the action of fluid passing through the joint capsule. Thus, there is a need to replenish fluid supplies easily and automatically reducing interaction by the staff and reducing the risk of operative joint collapse.

SUMMARY

In one aspect, a fluid (e.g., a liquid) source management system (which can be used during a surgical procedure) is disclosed whereby two or more fluid sources (herein also referred to as fluid containers), such as I.V. bags are attached to a frame (herein also referred to as a support structure), and the flow of the fluid out of those bags to a surgical site can be controlled so as to ensure that sufficient fluid is delivered to the surgical site during a surgical procedure. In some embodiments, each I.V. bag can be connected to a common fluid reservoir via a tubing. The tubing can include an inner lumen through which the fluid from the I.V. bag can be transferred, e.g., under the force of gravity, to the common fluid reservoir (herein also referred to for brevity as "common reservoir"). The common reservoir may have output connections to which tubing can be attached at one end with the other end being passes through an orthopedic pump (typically a peristaltic pump) which can operate to continuously push fluid through the instrumentation or an inserted trocar into the operative joint capsule.

In some embodiments, the system can selectively and independently adjust the flow rate including starting and stopping flow of the fluid from each of the I.V. bags to the common fluid reservoir, e.g., by closing off a portion of the lumen of the tubing to stop any fluid flowing from the I.V. bag through the tubing to the common reservoir, or maintaining the lumen in an open state to allow continued delivery of the fluid to the common reservoir. As discussed in more detail below and by way of example, in some embodiments, the lumen of a tubing connected to an I.V. bag that is not in use can be closed (e.g., choked off) to retain the fluid within the bag while another I.V. bag supplies the requisite fluid to the surgical site.

The system can also selectively and independently release the pressure on the external surface of the tubing thereby allowing the tubing's inner lumen to open and thereby allowing fluid from the I.V. bag to flow to the common reservoir. The mounting apparatus may include a central strut and at least two arms. The arms of the mounting apparatus may have a weight sensor or switch that continuously monitors the mass or weight of the I.V. bags that are suspended from it. When the weight sensor detects a weight below a minimum threshold (indicating diminished fluid volume) the system can selectively allow the opening of the lumens of tubing attached to an I.V. bag that has sufficient fluid thus allowing it to feed fluid into the common reservoir while simultaneously closing the lumens of the tubing connected to the depleted I.V. bag. The tubing used in the system may have connections common to standard I.V. bags. The output connector from the common reservoir may also mimic the output connections common to standard I.V. bags. Use of common connections allows standard orthopedic tubing as well as standard pumps (with the same common connection) to be used in the system.

The system allows for the automatic replacement of fluid flow from fluid supply bags containing a sufficient amount of fluid (e.g., full fluid supply bags) for those that do not contain a sufficient amount of fluid (e.g., the empty bags) and for continuous replenishment of fluid to the common reservoir and thence to the orthopedic pump. By way of example, once the fluid contained in an I.V. bag supplying fluid to the common reservoir is sufficiently depleted (e.g., when the I.V. bag is empty), the system may close the tubing to this bag without interfering with flow of fluid from a full I.V. bag also attached to the common reservoir. Any bags that become empty can be replaced by the staff at a convenient time (if required). The automatic replenishment of fluid allows maintaining a continuous fluid source for the orthopedic pump thereby reducing the number of interventions required by the staff for this task and also reducing the risk of an inadequate fluid flow during the surgical procedure, which may lead to the collapse of the operative joint capsule during the procedure.

In some embodiments, in order to measure fluid supply in a source (e.g., a liquid container such as an I.V. bag), the system can employ a spring-loaded mechanical switch on the hanging structure that may engage the tubing when the volume in the I.V. bag drops below a certain fluid threshold. The volume in the I.V. bag can be measured by weight of the fluid or by other methods, such as those described below. By way of example, this fluid threshold could be around 50 ml of fluid, below which the amount of the fluid in the bag may not be sufficient to sustain the requisite flow rate of the fluid to the surgical site. When the volume of the fluid within an I.V. bag drops below the fluid threshold, the system can engage a switch that signals an affector or other mechanical device to close off the inner lumen of tubing attached to the empty I.V. bag. Then, the system can simultaneously signal to the controller to release another affector thereby allowing the opening of the lumens of a tubing connected to an I.V. bag with available fluid.

Alternatively, an electronic analog force gauge can be used to signal that a fluid source is depleted below the threshold (e.g., it is empty) or that there is fluid available from a fluid source.

Other ways of determining fluid volumes in a fluid source may include photo-electronic eyes, capacitive switches and/or strain gauges which could be used to signal that a fluid source is depleted below the threshold (e.g., it is empty) or that there is fluid available from a fluid source.

In some embodiments, the fluid flow in a tubing can be stopped by mechanically squeezing the external surface of the tubing with an affector, thereby occluding the inner lumen of the tubing and thus constricting or stopping the flow of the fluid. This can be accomplished by any device such as solenoids, cams, linear actuators, or air powered cylinders that mechanically exerts pressure on the external surface of the tubing and temporarily constricts or occludes the lumen(s) of the tubing since tubing typically used may be constructed from elastic polymers. The inner lumens of the tubing can be opened by releasing the pressure on the tubing's external surface thereby allowing fluid to flow freely from the fluid source to the common reservoir.

The system may have indicators showing the fluid state of each I.V. bag. For example, such indicators can provide visual and/or audible signals, or other types of signals, indicative of the fluid state in respective I.V. bags, e.g., whether the I.V. bag (or a different fluid source) is empty, completely full or contain sufficient fluid to feed the common reservoir. For example, such fluid states of an I.V. bag can be indicated as full, adequate, or empty.

The common reservoir may have connections allowing the attachment of tubing sets at one end thereof. The other end of such tubing may interact with an orthopedic (peristaltic) pump or other instrumentation and thence to the operative joint capsule. This common reservoir may be a rigid structure having an internal volume (e.g., a fixed internal volume) that allows for sufficient fluid to feed the orthopedic pump and/or instrumentation. The connections to and from the common reservoir can be configured to fit standard tubing commonly used to connect fluid sources to pumps or instrumentation during orthopedic or other procedures. Alternatively, the common reservoir can be in the form of a flexible chamber, e.g., constructed of a malleable material, for example it can emulate an I.V. bag in material and construction with multiple inlets for connection of tubing to a fluid source and with a connection out to the orthopedic pump or instrumentation. The reservoir can be made of a material that is capable of being sterilized as are the connecting fluid source tubing sets.

The fluid source tubing may interact with the system through an adapter bay built into tubing support structure that allows engagement of the tubing with the system. In some implementations of such an embodiment, the system has two tubing acceptance bays although more than two tubing acceptance bays can be used. Each tubing acceptance bays can have one or more mechanical on/off affectors which interact with the system controller. These affectors can have two states including the closed state whereby the affectors close the tubing lumens and an open state whereby the affectors do not interact with the tubing lumens, thereby allowing them to be open. An adapter block may encapsulate the tubing and may be sized to mate closely into the acceptance bay. The adapter block may have mating features which allows it to lock into the tubing acceptance bay. The adapter block locates the tubing in the proper location of the tubing acceptance bay so that it can interface with the one or more affectors of the acceptance bay. The adapter block can have at least one window allowing the one or more affectors to interact directly with the external surface of the tubing. If the adapter block is not seated into the tubing acceptance bay, the system can signal to the controller that the bay is not available. It is understood that although this embodiment uses affectors to mechanically close the tubing other embodiments might use a blunt finger that presses against an opposing block or blunt pinchers that close on each other.

The hanging structure communicates the state of the fluid source (empty, full, or adequate) with the controller via communication wiring which may be located in internal channels in said structure. The controller may have a rechargeable power source such as a lithium battery and may include an outlet for a cord for attaching to an external power source for battery charging. It may also include a cord receptacle and/or a power cord for an external power supply to power the system. The cord may be attachable to a 100 V, 110V or 240V or other power outlets common to operating room theaters. The controller communicates with the tubing acceptance bay via communication wiring and can determine which affectors in a bay are in the open state and which affectors in the tubing acceptance bays are in the closed state.

In some embodiments, affectors located in the tubing acceptance bay may be in line with a linear actuator housed in the support structure. The linear actuator may connect to a power source in the controller through communication wires located in channels on the interior of the tubing support structure and the central strut. The adapter block can include fittings which can removably connect the adapter block to an interface in the tubing acceptance bay. The adapter block can encapsulate a portion of the tubing and can have at least one aperture sized to allow the one or more affectors in the tubing acceptance bay to press on the external surface of the tubing and occlude its lumen. When the one or more affectors in a tubing acceptance bay are in the closed state, the one or more affectors press against the external surface of that tubing thereby occluding its lumen and preventing any flow of fluid through it. When an affector in the tubing acceptance bay is in the open state, it releases any pressure on the external surface of the tubing thereby opening the lumen and allowing fluid flow through the tubing set.

BRIEF DESCRIPTION OF THE DRAWINGS

FIGS. 3A-3B illustrates aspects of a tubing support structure of an embodiment of a fluid source management system.

FIGS. 12A-12C illustrate one embodiment of a tubing support structure and adapter blocks.

DETAILED DESCRIPTION

It will be appreciated that for clarity, the following discussion will explicate various aspects of embodiments of the present disclosure, while omitting certain specific details wherever convenient or appropriate to do so. For example, discussion of like or analogous features in alternative embodiments may be somewhat abbreviated. Well-known ideas or concepts may also for brevity not be discussed in any great detail. One of ordinary skill will recognize that some embodiments of the present disclosure may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

As used herein, the terms "about" and, "substantially, and "substantially equal" refer to variations in a numerical quantity and/or a complete state or condition that can occur, for example, through measuring or handling procedures in the real world; through inadvertent error in these procedures; through differences in the manufacture, source, or purity of compositions or reagents; and the like. Typically, the terms "about" and "substantially" as used herein means 10% greater or lesser than the value or range of values stated or the complete condition or state. For instance, a value of about 10 or substantially equal to 10 can mean a concentration between 9 and 11. The terms also refer to variations that would be recognized by one skilled in the art as being equivalent so long as such variations do not encompass known values practiced by the prior art.

As used herein the term "and/or" includes any and all combinations of one or more of the associated listed items and may be abbreviated as "/".

Figure 1:
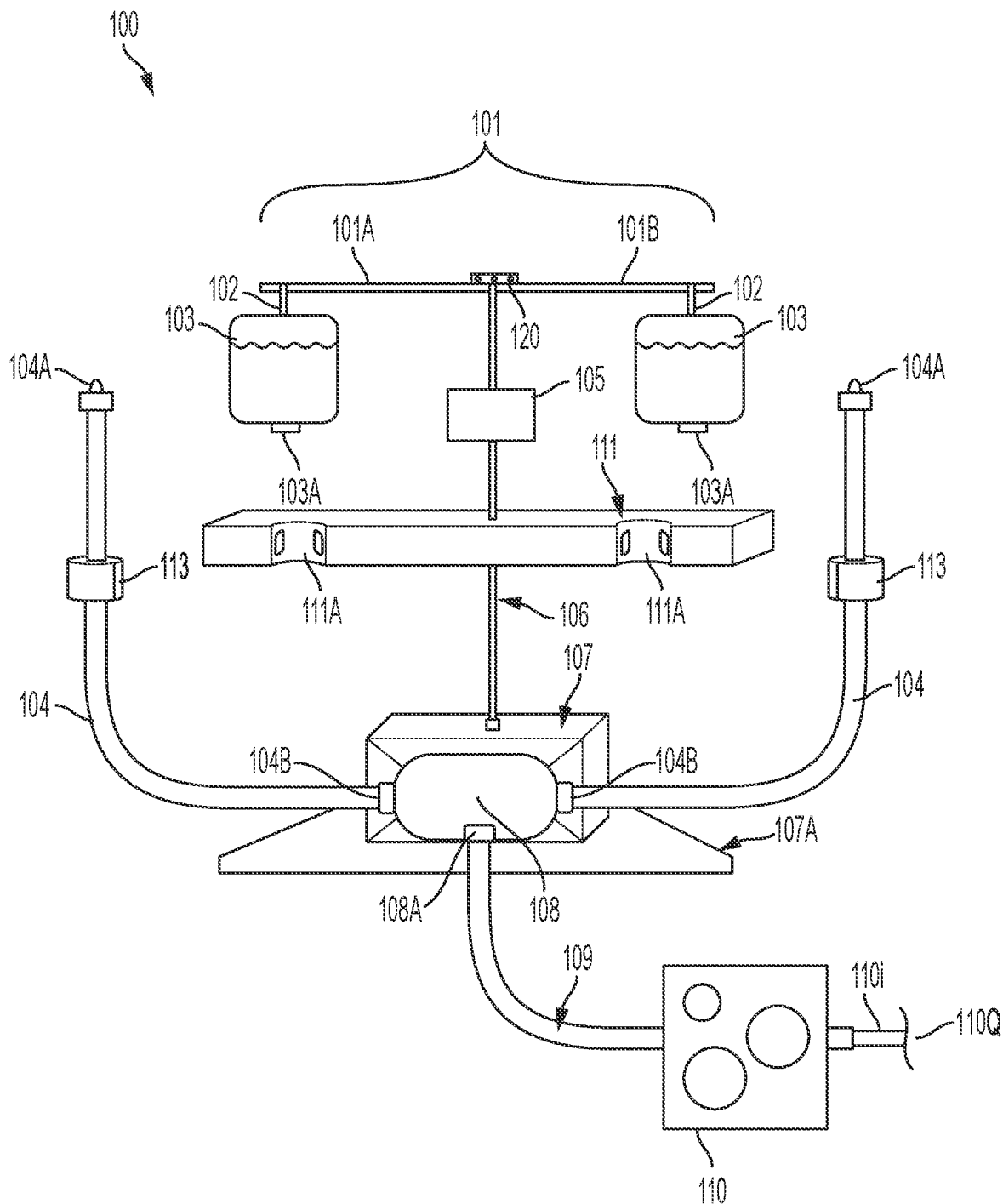
FIG. 1 illustrates one embodiment of a fluid source management system.

FIG. 1 illustrates one embodiment of a fluid source management system 100 comprising fluid sources 103 for supplying fluid to a reservoir 108. The fluid sources 103 can contain any type of fluid including, but not limited to normal saline, d5w solution and lactated ringers, and can be in the form of any type of container that can contain a fluid, such as an I.V. bag formed of elastic polymer. Other fluid containers in the system could included those formed or constructed out of metal, glass or plastic. The fluid source management system 100 also comprises tubing 104 that connects the fluid sources 103 to a fluid reservoir 108. In FIG. 1, the tubing 104 is not connected to fluid sources 103, but would be connected to the fluid sources 103 during normal operation. In this embodiment the system has two fluid sources 103 but in other embodiments it may have more than two fluid sources. Structure 101 has arm 101A and arm 101B to which the fluid sources 103 can be coupled (e.g., the fluid sources 103 may be hung from the arms 101A/101B using any device such as a hanger, ring, or hook). Sensors 102 are used to sense the amount of fluid remaining in the fluid sources 103. Sensor 102 can be any device that can sense the amount of fluid in the fluid sources 103, such as, but not limited to, a spring-loaded mechanical switch, an electronic analog force gauge, photo-electric sensor or a strain gauge that senses the weight of fluid source 103. Sensor 102 is in communication with controller 105 via internal wiring (not shown). Fluid source 103 can include output connector 103A. Controller 105 is in communication with tubing acceptance bay 111A by means of communication wiring (not shown) which may be located in an inside channel (not shown) in central strut 106 and also through an internal channel in tubing support structure 111.

Controller 105 may have a rechargeable power source (not shown) such as a lithium battery. It may also have a connection allowing the use of an external power source by means of connecting a power cord to a 110V or 240V power outlet common to operating room theaters. Controller 105 can be any type of microprocessor such as, but not limited to discontinuous controller, two position controller, programmable logic controller, a controller with embedded software. Central strut 106 attaches to reservoir housing 107 which is supported by stabilizer 107A. The reservoir housing 107 houses reservoir 108. Reservoir 108 can be any type of reservoir, such as flexible common reservoir 108. Input connectors 104B connect with system tubing 104 and output connecters 108A which connect with pump tubing 109 that in turn passes through and interacts with pump 110 which can be a peristaltic pump (not part of the system). Output tubing 110i (which is not part of the system) is the part of tubing 109 which passes through pump 110 and channels fluid to the operative site 110Q (not shown). Although one reservoir is shown, more than one reservoir could be used. Tubing 104 can be encapsulated in adapter block 113 (see FIG. 4) and can include connector 104A which is capable of being fitted into output connector 103A of fluid source 103. This embodiment includes visual indicator 120 that indicates the status of the total state of fluid sources in the system 100. For example, as described below with reference to FIG. 5A and FIG. 5C, lights can be used to indicate the status of the state of fluid in the fluid sources 103.

Figure 2:
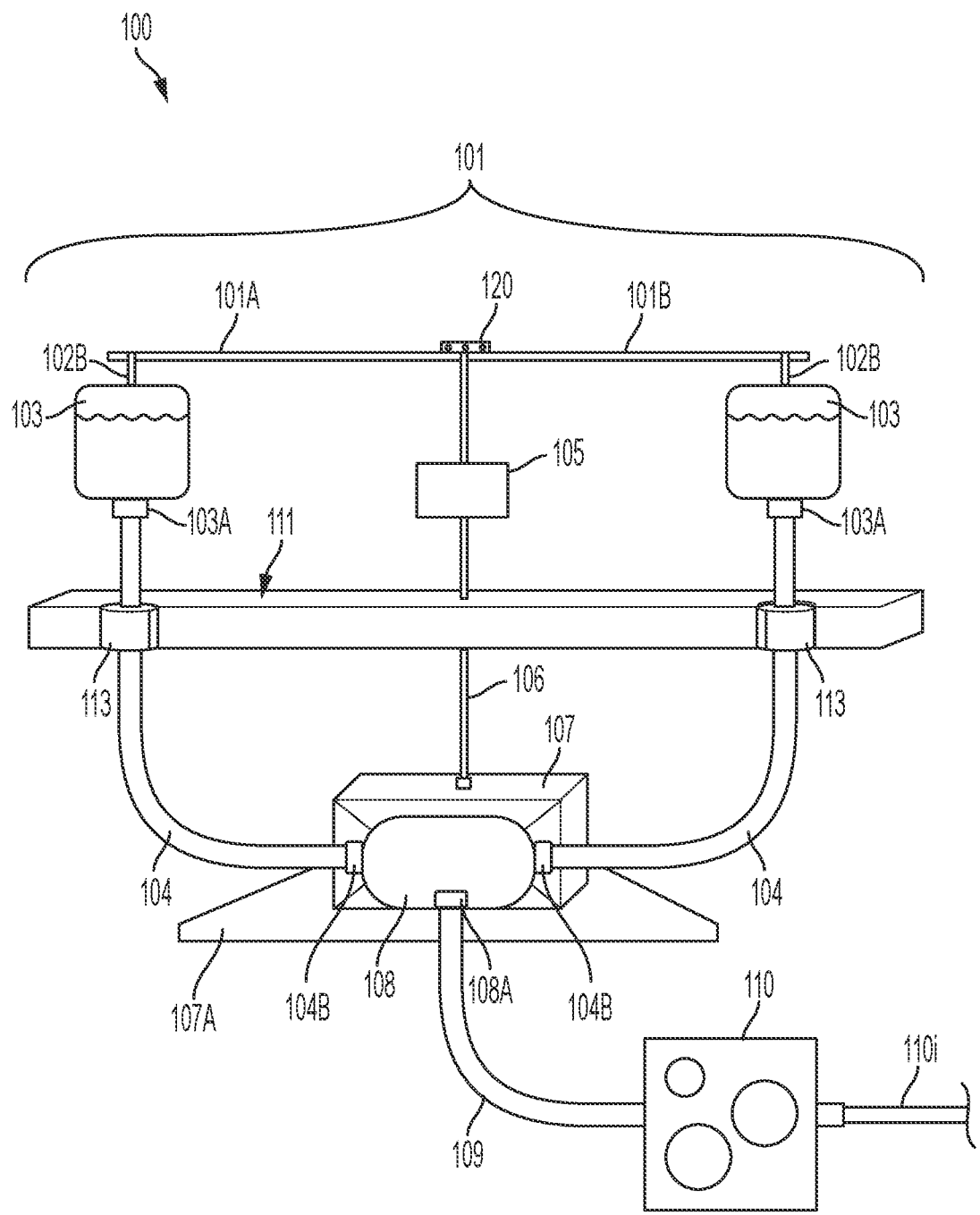
FIG. 2 illustrates another aspect of an embodiment of a fluid source management system.

FIG. 2 illustrates another aspect of fluid source management system 100 with system tubing 104 connected to fluid sources 103. In this embodiment the system has two fluid sources 103 but in other embodiments it may have more than two fluid sources. Structure 101 has arm 101A and arm 101B by which fluid sources 103 may be hung from hanger with sensor 102B coupled between the arm. Hangers with sensor 102B may include a spring loaded mechanical switch. In other embodiments hanger with sensor 102B may include electronic analog force gauge or a strain gauge to sense the weight of fluid source 103. Hanger sensor 102B is in communication with controller 105 via communication wiring (not shown). Fluid sources 103 has output connectors 103A. Controller 105 is in communication with tubing acceptance bay 111A by means of communication wiring (not shown) which runs down central strut 106 and through tubing support structure 111. Central strut 106 attaches to reservoir housing 107 which is supported by stabilizer 107A.

Flexible common reservoir 108 has input connectors 104B which connect with system tubing 104 and output connecters 108A which connect with pump tubing 109 that is in turn passes into and interacts with pump 110 which is typically a peristaltic pump. Pump tubing 110i interacts with the portion of pump tubing 109 that exits Pump 110 and provides a path for flow to the operative site (not shown) or to instruments used in procedure. In this embodiment, the common reservoir has two input connectors 104B but in other embodiments there may be three or more input connectors 104B. Tubing 104 is encapsulated by adapter block 113 (see FIG. 4A) and has connector 104A (see FIG. 1) which is capable of being fitted into output connector 103A of fluid source 103. Adapter block 113 fits into tubing acceptance bay 111A of tubing support structure 111 (see FIG. 1) and holds system tubing 104 in the appropriate place allowing the system to open and close the lumens of tubing 104 (see FIG. 3 and FIG. 4). Visual indicator 120 can include lights indicating the status of the total state of fluid sources in the system (see FIG. 5A and FIG. 5C).

FIG. 3A-3B illustrate one aspect of an embodiment of fluid source management system 100 from FIG. 1 and FIG. 2. Tubing support structure 111 is attached to central strut 106 (see FIG. 6). Communication wiring 111E from controller 105 (see FIG. 1 and FIG. 2) passes through the inside of central strut 106 to linear actuator 111D which is attached to affector 111B seated in tubing acceptance bay 111A. Hole 111Q allows egress and ingress of affector 111B to interact with the external surface of tubing 104 (not shown) thereby closing and opening fluid flow through the tubing 103. Tubing acceptance bay 111A has acceptance slot 111F formed in it along with platform 111G allowing snug and removable attachment of adapter block 113 (not shown see FIG. 1, FIG. 2, and FIG. 4).

When the volume of any of the fluid sources 103 (see FIG. 2) drops below a certain fluid threshold, the controller 105 (see FIG. 1) can create a signal that causes the affector 111B corresponding to the depleted fluid source 103 to close off fluid flow through the tube 103 connected to that fluid source 103. The controller 105 (see FIG. 1) can create a signal, e.g., before subsequent to, or concurrent with the closure of the tubing 103 to release another affector 111B thereby allowing the opening of a affector 111B corresponding to another fluid source 103 to open and thereby supply fluid from the other fluid source 103 to the common reservoir 108 while simultaneously closing the tubing of a depleted or almost empty fluid source. This fluid threshold could be around 50 ml of fluid for a fluid source, though other thresholds may also be used.

Figure 4A:
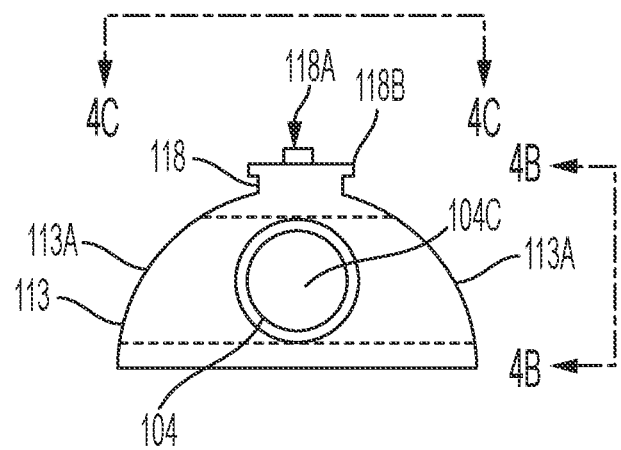
FIGS. 4A-4C illustrate aspects of an acceptance bay of an embodiment of a fluid source management system. an adapter block.
Figure 4B:
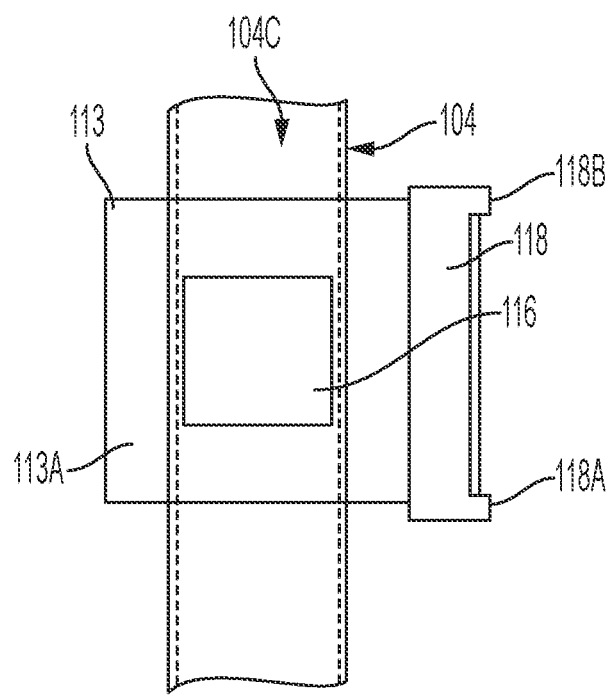
Figure 4C:
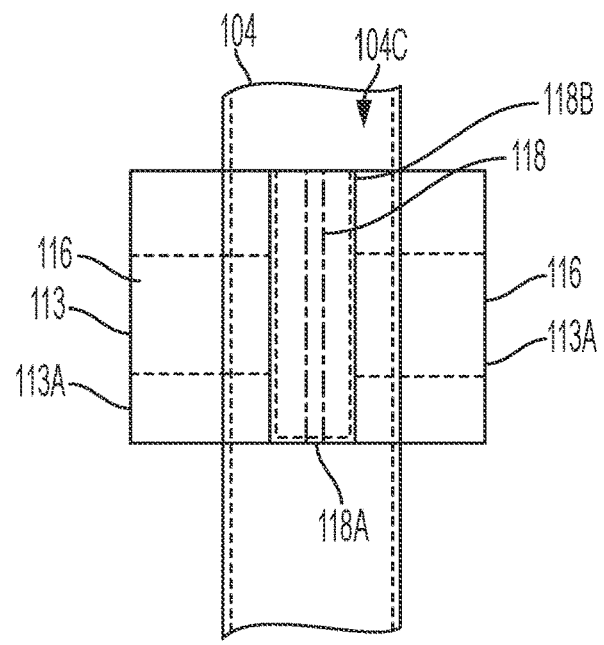

FIGS. 4A-4C are illustrations of another aspect of one embodiment of fluid source management system 100 from FIG. 1 and FIG. 2. A plan view of one embodiment of adapter block 113 with lateral sides 113A is shown in FIG. 4A. Adapter block 113 is sized to fit snuggly and removably into tubing acceptance bay 111A of FIG. 3B. Plug 118 has platform 118A and wings 118B with both features fitting snuggly into acceptance slot 111F and onto platform 111G (neither shown see FIG. 3). System tubing 104 with lumens 104C is encapsulated by adapter block 113. FIG. 4B illustrates section 4B-4B of FIG. 4A of adapter block 113. Adapter block 113 has aperture 116 formed into lateral sides 113 A of the adapter block. In an inactivated state, the affector 111B of FIG. 3A can be retracted (at least partially) into the adapter block, thereby allowing normal fluid flow through the tubing. Aperture 116 is sized to allow egress of affector 111B of FIG. 3A once the affector 111B of FIG. 3A is activated such that affector 111B of FIG. 3A can interact with the external surface of tubing 104, e.g., by applying an inward pressure on the external surface of the tubing, thereby constricting or occluding the tubing lumen and consequently the flow of the fluid through the lumen.

FIG. 4C illustrates section 4C-4C of FIG. 4A. Aperture 116 is formed into lateral sides 113A of adapter block 113. Plug 118 has platform 118A and wings 118B with both features fitting snuggly into acceptance slot 111F and onto platform 111G (see FIG. 3). System tubing 104 with lumens 104C, which are encapsulated by adapter block 113 pass through a hole formed in and through adapter block 113.

Figure 5A:
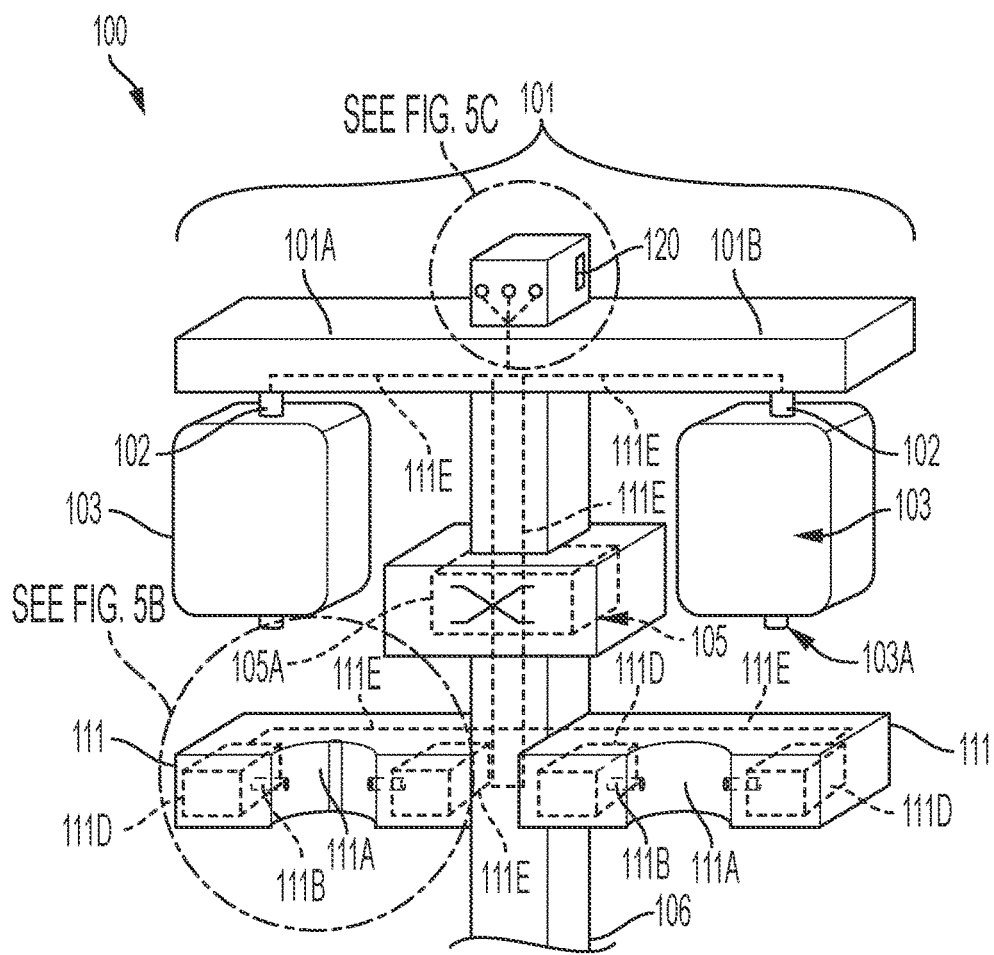
FIGS. 5A-5C illustrate aspects of a tubing support structure of an embodiment of a fluid source management system.

FIG. 5A is an illustration of aspects of one embodiment of fluid source management system 100 with system tubing 104 not connected and not shown (see FIG. 1 and FIG. 2). In this embodiment, the system has two fluid sources 103 but in other embodiments it may have more than two fluid sources 103. Fluid source management system 100 has arm 101A and arm 101B from which fluid sources 103 may be hung from hanger with sensor 102. Hangers with sensor 102 may include a spring load mechanical switch. In other embodiments hanger with sensor 102 may include electronic analog force gauge, photo-electric sensor, or a strain gauge to sense the weight of fluid source 103. Sensor 102 is in communication with controller 105 via communication wiring 111 E which passes through an internal channel in arm 101A and arm 101B and thence through an internal channel in central strut 106 to controller processor 105A.

Fluid source 103 has output connector 103A. Controller processor 105A is located in controller 105 and is in communication with tubing acceptance bay 111A by means of communication wiring 111E placed in an internal channel (not shown) in central strut 106 and in tubing support structure 111. Controller processor 105A may have a rechargeable power source (not shown) such as a lithium battery. It may also have a connection allowing the use of an external power source (not shown) by means of connecting a power cord to a 110V or 240V power outlet common to operating room theaters. Linear actuator 111D located inside tubing support structure 111 is attached to affector 111B located inside tubing support structure 111 and is in communication with controller processor 105A via communication wire 111E located in an internal channel of support structure 111.

Figure 5B:
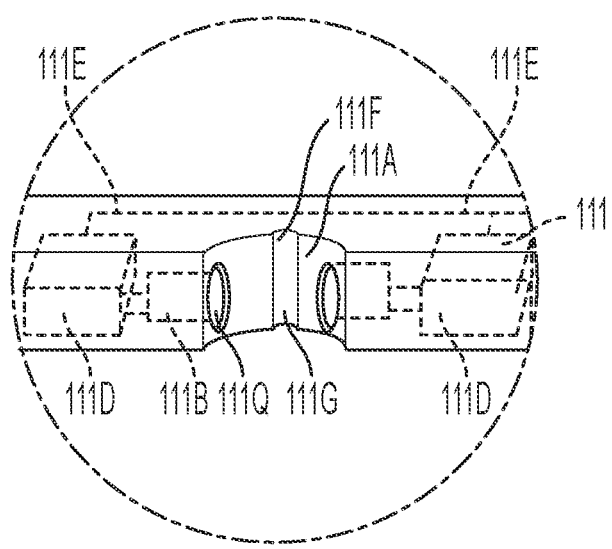

FIG. 5B shows details of the circular portion in FIG. 5A. Tubing support structure 111 has tubing acceptance bay 111A formed therein. Communication wiring 111E is located in an internal channel (not shown) of tubing support structure 111. Communication wire 111E connects linear actuator 111D to controller processor 105A. Linear actuator 111D is attached to affector 111B. Affector 111B is nested inside tubing support structure 111. Hole 111Q allows for egress of affector 111B into tubing acceptance bay 111A via the action of linear actuator 111D. Tubing acceptance bay 111A has acceptance slot 111F formed in it along with platform 111G to allow snug removable attachment of adapter block 113 (FIG. 1, FIG. 2, and FIG. 4).

Figure 5C:
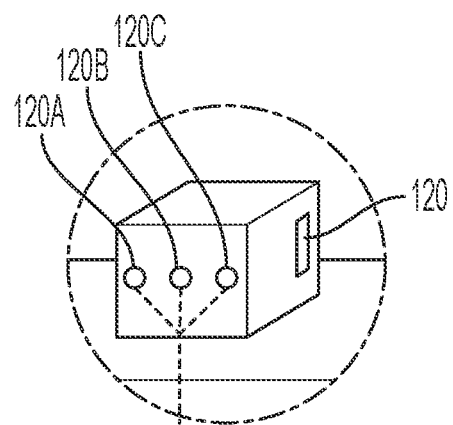

FIG. 5 C illustrates on embodiment of visual indicator 120 of system 100 of FIG. 1 and FIG. 2. Visual indicator 120 can comprise lights indicating the status of the total state of fluid of the system (see FIG. 5A and FIG. 5C) and is in communication with controller processor 105A and hanger with sensor 102 by means of communication wire 111E. In one embodiment visual indicator 120 light, 120A may be green and lit when all fluid sources are full, light 120B could be lit and yellow when one or more fluid sources are full while light 120C could be lit red when no fluid sources are full or available. Any other type of visual indicator can be used to indicate the fluid state of the fluid sources (103), such as, but not limited to, audible alarms, analog, or digital numeric displays.

Figure 6A:
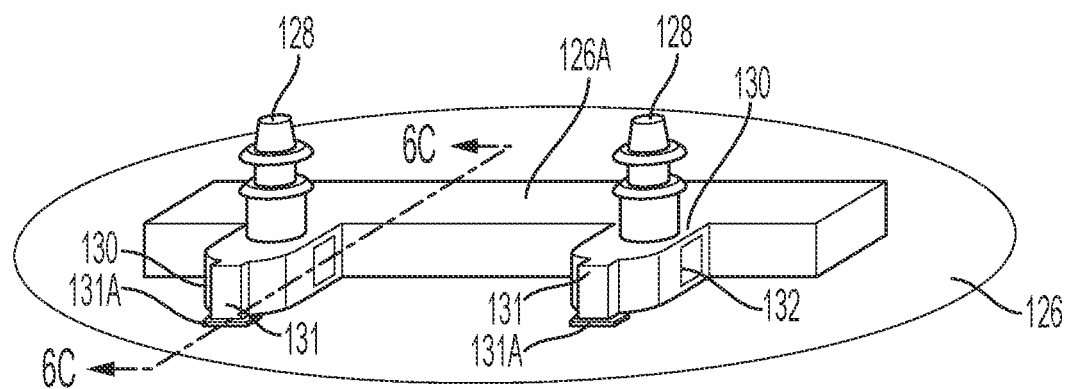
FIGS. 6A-6D illustrate another embodiment of a fluid source management system.
Figure 6B:
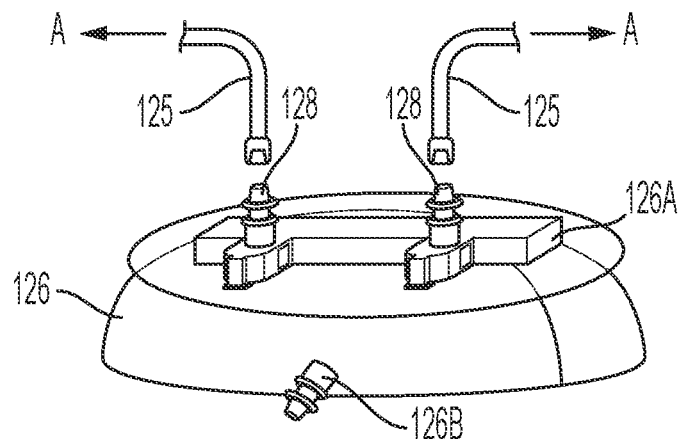
Figure 6C:
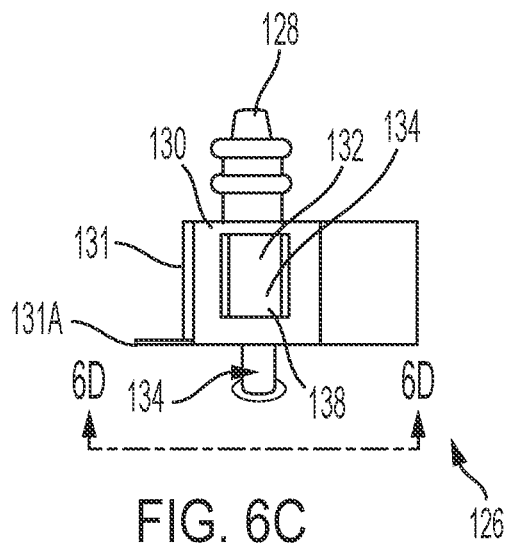

FIGS. 6A-6D show aspects of another embodiment of fluid source management system 100 of FIG. 1, FIG. 2, and FIG. 5. In this embodiment flexible reservoir 126 has connector manifold 126A formed in or attached to an upper surface of the reservoir 126. Details of an example connector manifold 126A are shown in FIG. 6A. Protuberances 130 are formed into one side of connector manifold 126A. This embodiment of manifold connector 126A has two protuberances 130 but in other embodiments more than two could be present. Aperture 132 is formed into the sides of protuberance 130. Plug 131 and platform 131A formed in protuberance 130 fit snuggly into a slot formed in acceptance bay 111A (see FIG. 7A and FIG. 7B) of tubing support structure 111 (not shown; see FIG. 7 and FIG. 7B). Acceptor nozzle 128 is formed into the upper outer surface of protuberance 130. Acceptor nozzle 128 is shown with a common male adapter formed into its end allowing it to fit into common female adapters formed in the end of common tubing 125. Any type of manifold could be used, such as a Qosina 4-Gang stopcock manifold (part number 17552).

Figure 6D:
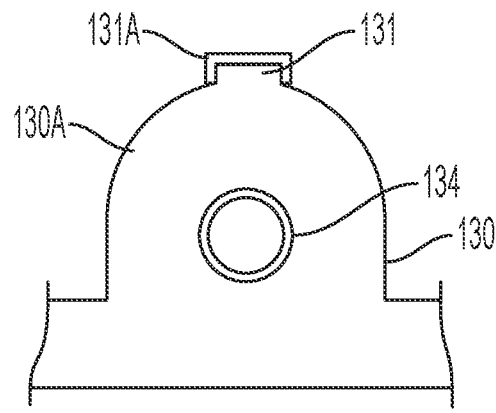

In other embodiments, the adapter formed into the end of acceptor nozzle 128 can be a female adapter that can be fitted around common male adapters formed or attached to the end of common tubing 125. Section 6C-6C (see FIGS. 6A and 6C) shows a cross section of connector manifold 126 A. In this cross-section, aperture 132 is formed into the side of protuberance 130 which allows affector 111B (see FIGS. 7A and 7B) of acceptance bay 111A (see FIGS. 7A and 7B) to access internal tubing 134. Internal tubing 134 is attached to the bottom of end of acceptor nozzle 128 and runs through a channel 130 out through the bottom of the protuberance 130 into flexible reservoir 126A. FIG. 6D (Section 6D-T6D in FIG. 6C) shows a plan view of the underside of connector manifold 126. Plug 131 with platform 131A is formed into the proximal side of protuberance 130. Internal tubing 134 protrudes downward from bottom surface 130A of protuberance 130 into the upper section of flexible reservoir 126A. Protuberance 130 has plug 131 with platform 131A formed thereon thereby allowing its secure and removable attachment into tubing acceptance bay 111A (see FIGS. 7A and 7B).

Figure 7A:
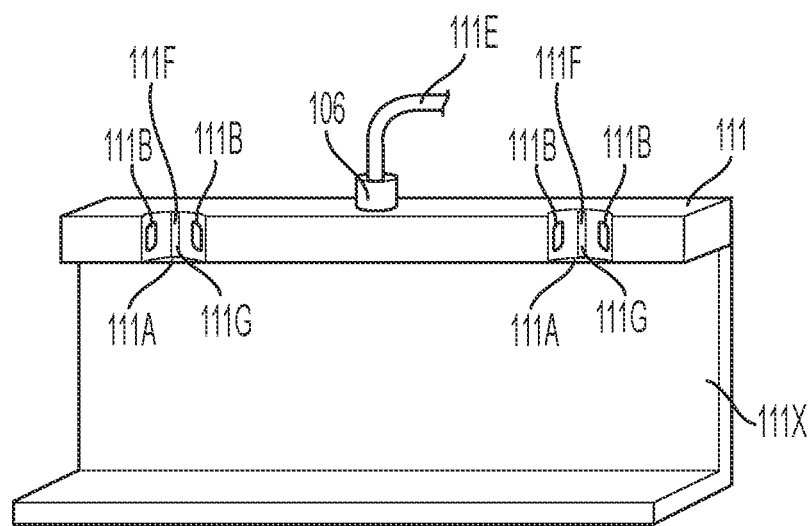
FIGS. 7A and 7B illustrate another embodiment of a fluid source management system.
Figure 7B:
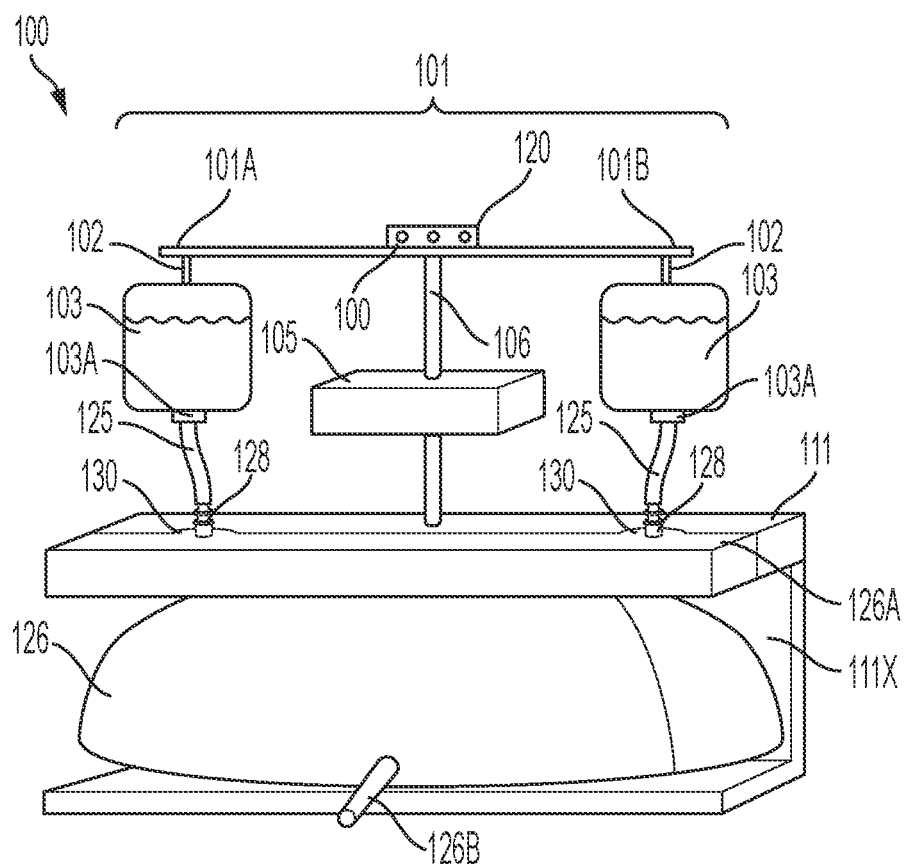

FIGS. 7A and 7B show details of another embodiment of fluid source management system 100. In this embodiment, structure 101 has arm 101A and arm 101B by which fluid source 103 may be hung from hanger with sensor 102 therebetween. In this embodiment two fluid sources are shown but in other embodiments there can be more than two fluid sources. Sensor 102 can include a spring load mechanical switch. In other embodiments, sensor 102 may include electronic analog force gauge or a strain gauge to sense the weight of fluid source 103. In this embodiment, sensor 102 is in communication with controller 105 via internal wiring (not shown). Fluid source 103 has output connector 103A which allows common tubing 125 to be attached thereto.

Controller 105 is in communication with tubing acceptance bay 111 by means of communication wiring (not shown) which may be located in an inside channel (not shown) within central strut 106 and or in an internal channel (not shown) in tubing support structure 111. Controller 105 may have a rechargeable power source (not shown) such as a lithium battery. It may also have a connection allowing the use of an external power source by means of connecting a power cord to a 110V or 240V power outlet common to operating room theaters. Visual indicator 120 has lights indicating the status of the total state of fluid of the system (see FIG. 5A and FIG. 5C) and is in communication with controller 105 and hanger with sensor 102 by means of communication wire (see FIGS. 5A and 5B).

Central strut 106 attaches to tubing support structure 111 with tubing acceptance bays 111A. In this embodiment, system 100 has two tubing acceptance bays but in other embodiments it may have more than two such bays. Connector manifold 126A is attached to or formed into the upper surface of flexible reservoir 126. Flexible reservoir 126 has tubing outlet connector 126B that can interact with a pump (not shown) through a tubing.

Shelf 111X is formed into the bottom of tubing support structure 111 and is designed to hold flexible reservoir 126 in place when system 100 is in use. Protuberances 130 can be designed to fit snuggly into tubing acceptance bays 111A. In this embodiment, two such bays are shown but there could be more than two bays. Protuberance 130 of manifold connector 126A has acceptor nozzle 128 formed into its upper surface. Acceptor nozzle 128 in this embodiment is a male adapter sized to fit the female connector of tubing 125 but in other embodiments it may be formed with a female adapter that allows it to be attached to common tubing 125.

FIG. 7A shows details of an embodiment of some aspects of tubing support structure 111 including shelf 111X which is designed to hold flexible reservoir 126 (see FIG. 7A). Tubing acceptance bay 111A has affector 111B in tubing support structure 111 (see FIG. 5A and FIG. 5B). Tubing acceptance bay 111A has acceptance slot 111F formed therebetween along with platform 111G to allow snug and removable attachment of protuberances 130 (see FIG. 5B) of connector manifold 126A (not shown see FIG. 6A). Central Strut 106 is attached to tubing support structure 111. Communication wires 111E located in internal channels in tubing support structure 106 and connection manifold 126A connect tubing support structure 126A with controller 105 (see FIG. 5A and FIG. 5B).

Figure 8A:
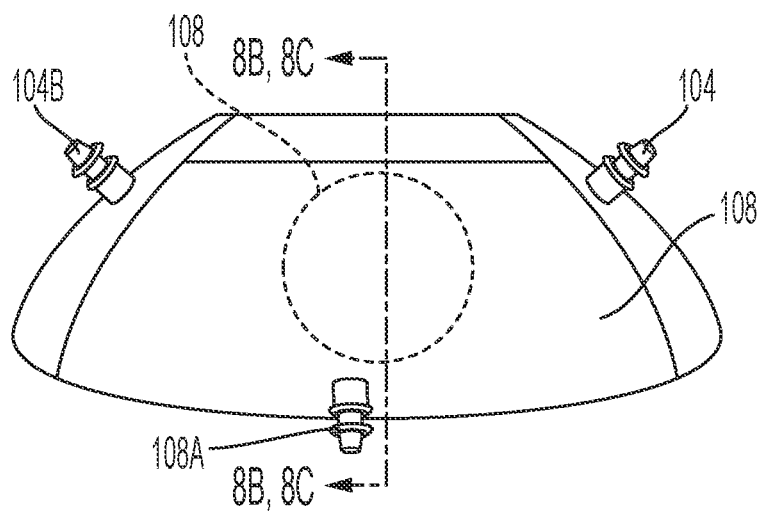
FIGS. 8A-8C illustrate aspects of a flexible reservoir of an embodiment of a fluid source management system.
Figure 8B:
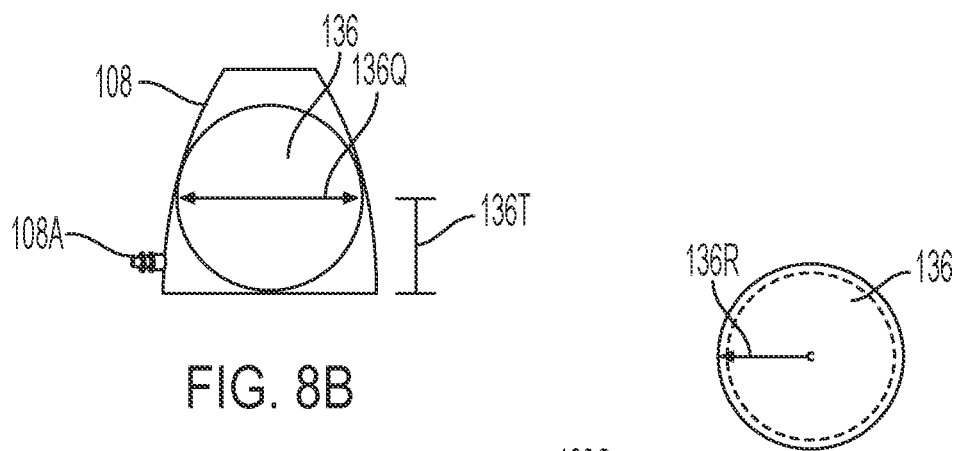

FIGS. 8A-8B show aspects of one embodiment of flexible reservoir 108 of fluid source management system 100 of FIG. 1. In this embodiment flexible reservoir 108 has input connector 104B formed into its sides allowing common tubing 104 of FIG. 5 to be attached thereto. In this embodiment, there are two input connectors, but there may be more than two input connectors.

By way of example, flexible reservoir 108 can be formed of non-reactive hemo-compatible materials commonly used in I.V. bags including soft plastic or vinyl materials including those made of PVC or polypropylene. The volume of flexible reservoir 108 could range from about 0.25 liters to about 4 liters. In some embodiments, a structure 136, such as a hollow sphere, which can be made of an inert material such as plastic, can be located inside flexible reservoir 108 shown in FIG. 8B. The structure 136 can be formed into any three-dimensional shape or polygon.

Hollow sphere has radius 136R (see FIG. 8C) which is equal to half of the distance 136Q. Distance 136T is measured from the bottom surface of the inside of flexible reservoir 108 and is equal to ½ of 136Q. Hollow sphere 136 prevents flexible reservoir 108 from collapsing on itself.

Figure 8C:
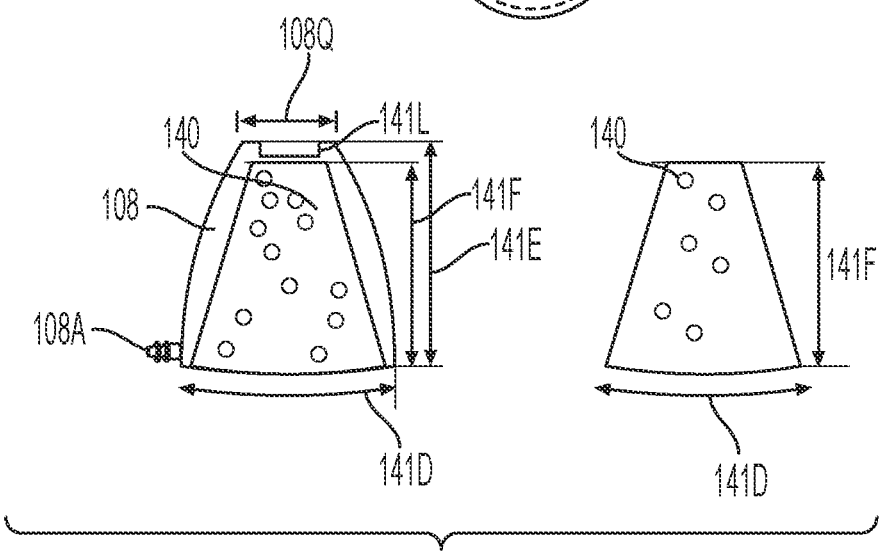

In another embodiment shown in FIG. 8C, foam block 140 is positioned inside flexible reservoir 108. Foam block may be formed and comprised of a thin membrane of polyurethane encapsulating a network of open cell foam producing an open-pore reticulated foam with a skeletal structure through which fluids easily pass. In some embodiments, foam block 140 may be formed of open cell foam formed of polyethylene or polyester or a combination of these materials. Pore sizes in these embodiments can range from about 4 to about 100 pore per inch with foam block 140 possessing void volumes of up to about 98% and surface areas of up to about 2,000 sq. ft. per cubic foot.

In the embodiment shown in FIG. 8C, foam block 140 has a height of 141F which is equal to about 90% of height 141E of flexible reservoir 108. The width of the base of foam block 140 is about equal to the width 141D of the base of flexible reservoir 108. Width 141L of the top of foam block 140 is equal to about 75% of width 141D of flexible reservoir 108. Foam block 140 prevents flexible reservoir 108 from collapsing onto itself.

Figure 9A:
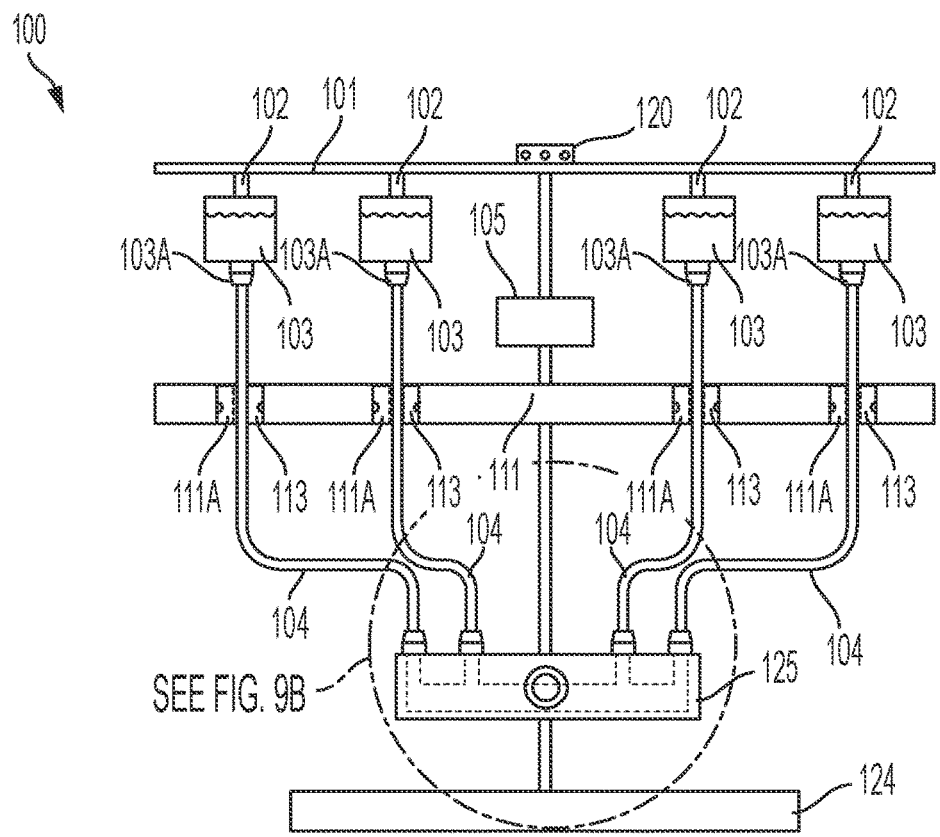
FIGS. 9A-9B illustrate aspects one embodiment of a fluid source management system.

FIG. 9A illustrates another embodiment of a fluid source management system 100 comprising fluid sources 103 for supplying fluid to a manifold 125. The fluid sources 103 can provide any type of fluid including, but not limited to normal saline, d5w solution and lacted ringers. Fluid source management system 100 also comprises tubing 104 that connects the fluid sources 103 to manifold 125. In this embodiment one manifold is shown but in other embodiments there could be more than one manifold. In FIG. 9A, tubing 104 is connected to fluid source 103 and to manifold 125. In this embodiment the system has four fluid sources 103 but in other embodiments it may have more two or more fluid sources. Structure 101 has arm 101A and arm 101B by which fluid sources 103 may be hung using any device such as a hanger or hook. Sensors 102 are used to sense the amount of fluid remaining in fluid sources 103. Sensor(s) 102 can be any device that can sense the amount of fluid in the fluid sources 103, such as, but not limited to, a spring-loaded mechanical switch, an electronic analog force gauge, a photo-electric sensor or a strain gauge that senses the weight of fluid source 103. Sensor(s) 102 is in communication with controller 105 via internal wiring (not shown). Fluid source 103 can include output connector 103A. Controller 105 is in communication with tubing acceptance bays 111A by means of communication wiring (not shown) which may be located in an inside channel (not shown) in central strut 106 and also through an internal channel in tubing support structure 111.

Central strut 106 attaches to manifold 125 and also to support base 127. Controller 105 may have a rechargeable power source (not shown) such as a lithium battery. It may also have a connection allowing the use of an external power source by means of connecting a power cord to a 110V or 240V power outlet common to operating room theaters. Controller 105 can be any type of microprocessor such as, but not limited to discontinuous controller, two position controller, programmable logic controller, a controller with embedded software. Manifold 125 has four inlets 126 in this embodiment but in other embodiments it could have two or more inlets 126. Inlet 126 has a connector which allows tubing 104 to be attached that allows fluid to flow through tubing 104 from fluid source 103 through to manifold 125.

Figure 9B:
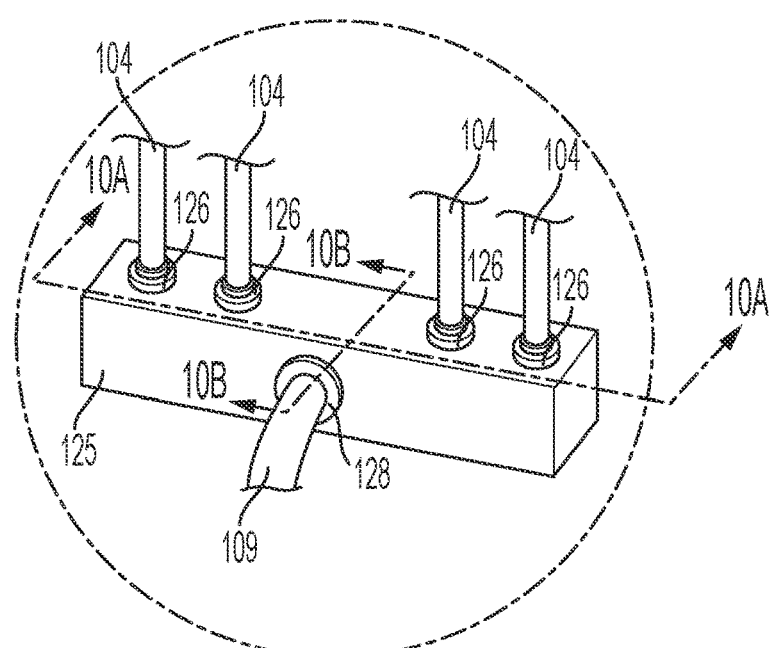

FIG. 9B shows some aspects of manifold 125 including inlet 126 with tubing 104 attached to it. This embodiment has four inlets 126 but other embodiments could have two or more inlets 126. In this illustration, manifold 125 has one outlet 128 but other embodiments there may be more than one outlet 128. The distal end of outlet tubing 109 is connected to outlet 128 of manifold 125. The proximal end (not shown) of outlet tubing 109 is interacts with and passes through to pump 110 (not shown). In this embodiment manifold 125 is rectangular in shape but in other embodiments if could be square, round, obolid or other suitable geometric shapes. Manifold 125 can be formed of suitable waterproof material including metal, rubber, plastic, or a combination of these materials.

Figure 10A:
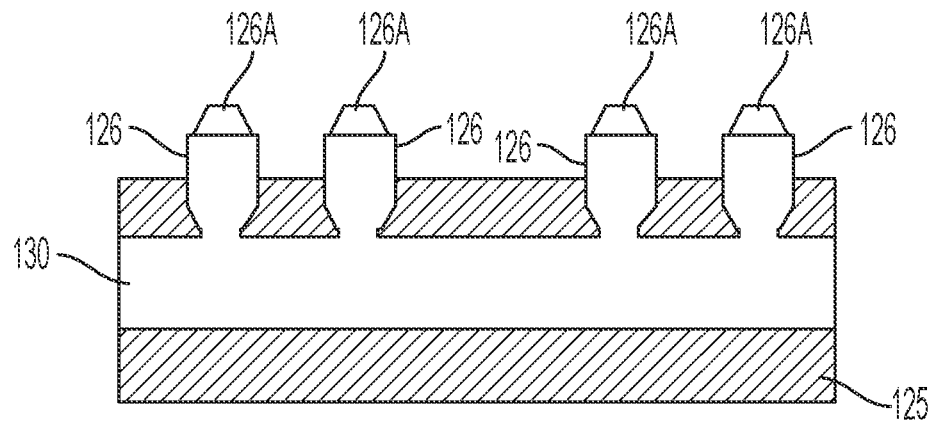
FIGS. 10A-10B illustrates aspects of a manifold of an embodiment of a fluid source management system.
Figure 10B:
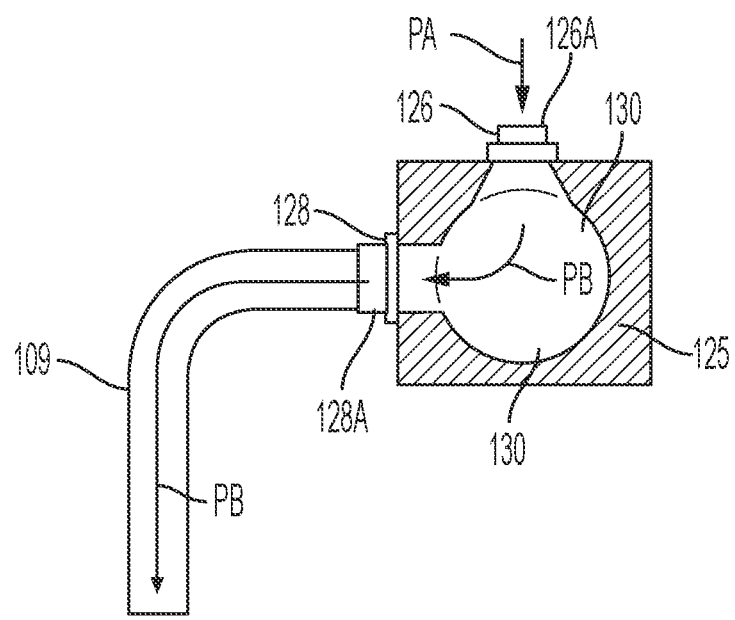

FIGS. 10A and 10B illustrate certain aspects of FIG. 9A including section 10A-10A (see FIG. 9B) and section 10B-10B (see FIG. 9B), respectively, that provide certain cross-sectional views of this embodiment of manifold 125. Section 10A-10A of FIG. 10A illustrates flow chamber 130 which runs the length of the interior of manifold 125. Manifold 125 includes inlet 126 with connecter 126A which allows tubing 104 to be connected to manifold 125. The interior of inlet 126 opens into flow chamber 130 as shown in FIGS. 10A and 10B. This embodiment includes four inlets 126 but other embodiments could include two or more inlets 126.

Section 10B-10B of FIG. 10B provides another cross-sectional view of manifold 125. Inlet 126 has connector 126A which allows tubing 104 (not shown) to be connected to it. The interior of inlet 126 opens up into flow chamber 130. Outlet 128 has connecter 128A attached thereto that allows the distal end of outlet tubing 109 to be connected to the outlet 128. Proximal end of outlet tubing 109 connects to pump 110 (not shown). Outlet 128 opens up into flow chamber 130 of manifold 125. Flow of fluid from the fluid source (not shown) through tubing (not shown) flows into inlet 126 in the direction of arrow PA and then into flow chamber 130 of manifold 125. Fluid entering flow chamber 130 from inlet 126 then flows into the interior of outlet 128 with connecter 128A into attached outlet tubing 109 in the direction of arrow PB and from there into pump 110 (not shown).

Figure 11A:
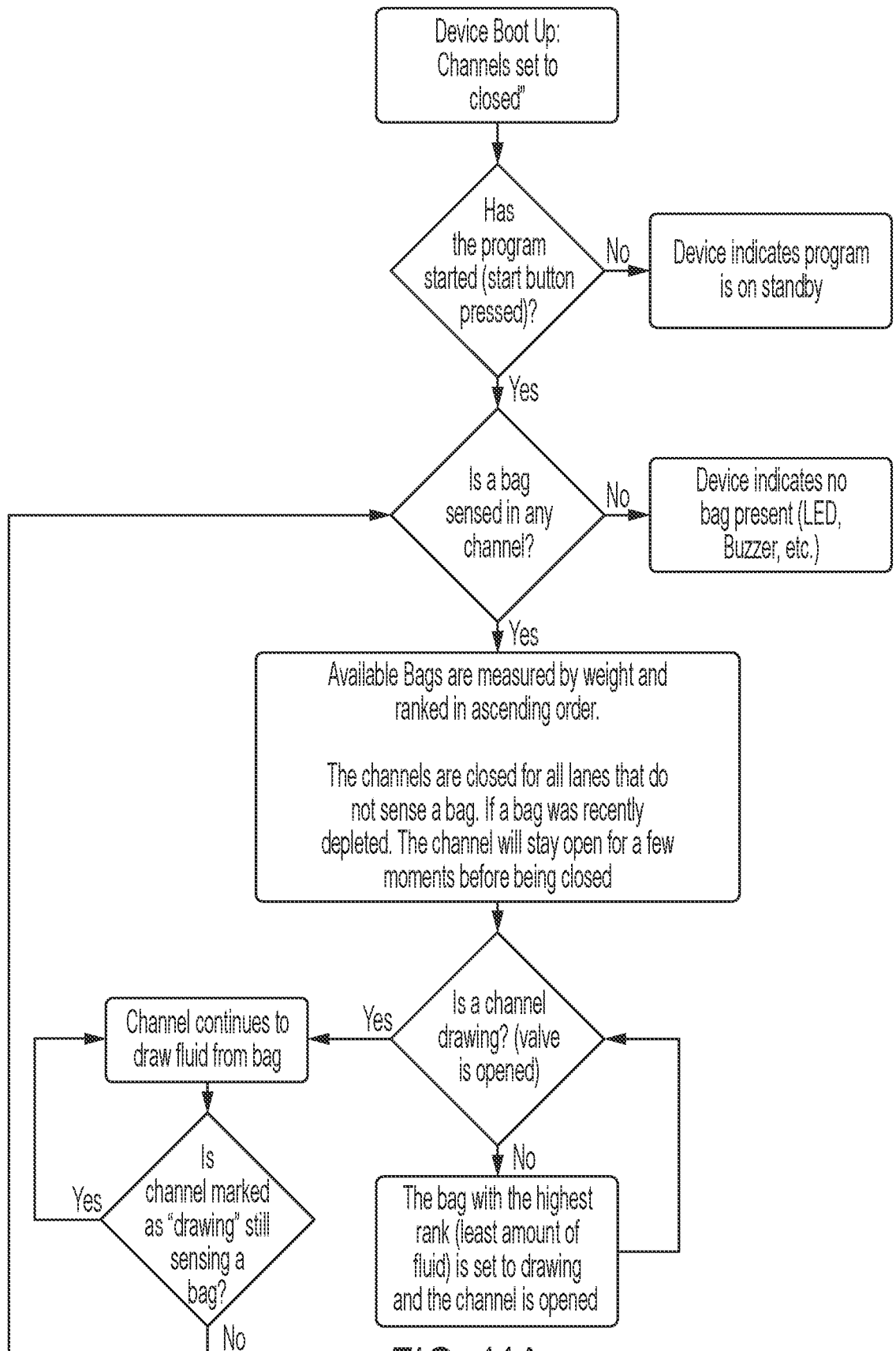
FIGS. 11A-11C illustrate aspects of decision logic used in an embodiment of a fluid source management system.

FIGS. 11A-11D provide some details of the logic that can be used in at least one embodiment of the fluid source management system including determining how and when tubing connected to a fluid source may be closed or left open and in which sequence and when certain indicators may be activated (including "no source present", "empty connector bay," and "device on standby"). In FIG. 11A, all possible fluid sources are referred to as "Channels." As shown in FIG. 11A, during device Boot Up, all of the Channels are set to a closed (Step 100) status. After device Boot Up, the logic senses whether the program has started (i.e., whether the start button has been pressed) (Step 101). If the start button has not been pressed, the system indicates that the program is in Standby mode (Step 102). If the start button has been pressed, the program checks whether any of the available fluid sources (e.g., I.V. bags) have been sensed in any of the channels (Step 103). If no fluid sources are sensed, the system indicates that no bags are present (Step 104). This can be done by lighting an LED light or sounding an alarm, buzzer, etc. If at least one fluid source is sensed, the fluid content of the available fluid sources are measured by weight and ranked in ascending order (Step 105). Also, in Step 105, the Channels are closed for all lanes that do not sense a fluid source, and if a fluid source was recently depleted, the channel for that fluid source can stay open for a small amount of time (e.g., 30 seconds) before being closed. The next step in the logic shown in FIG. 11A is to check whether a channel is drawing fluid (i.e., whether the affector controlling fluid flow from the fluid source is opened) (Step 106). If the Channel is not drawing fluid, the fluid source with the highest rank (i.e., least amount of fluid) is set to drawing fluid and the Channel is opened (Step 107). If the Channel is drawing fluid, the Channel continues to draw fluid from the fluid source (Step 108). After Step 108, it is determined whether the Channel marked as drawing a fluid still senses a bag (Step 109). If the Channel marked as drawing a fluid still senses a bag (i.e., "Yes" in Step 109), the logic moves back to Step 108 so that the Channel continues to draw fluid from the fluid source. If the Channel marked as drawing a fluid does not sense a bag (i.e., "No" in Step 109), the logic moves to Step 103 (i.e., the program checks whether any fluid sources (e.g., I.V. bags) have been sensed in any of the channels).

Figure 11B:
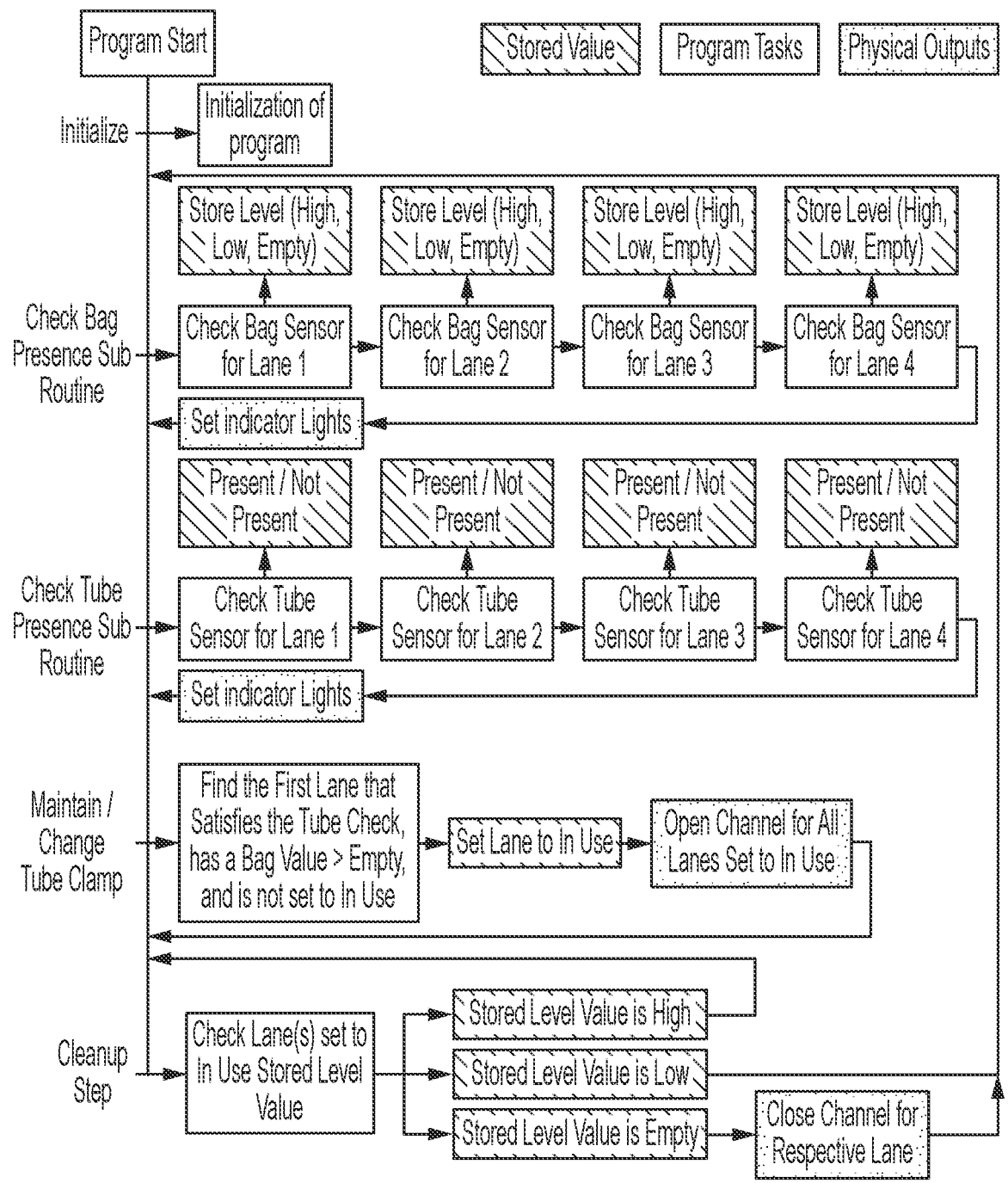
Figure 11C:
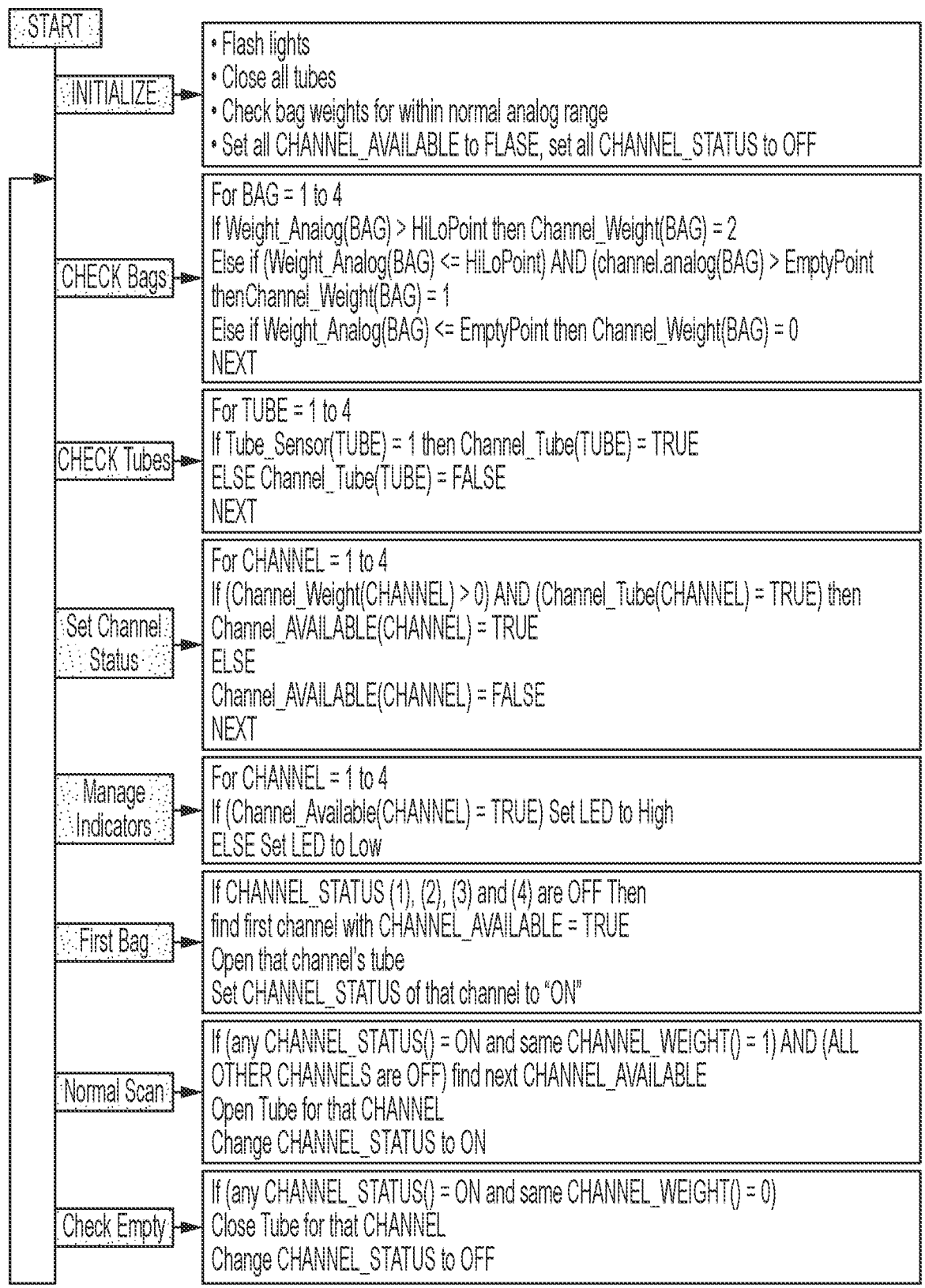

FIGS. 11B and 11C illustrate some details of the logic that can be used upon start up in at least one embodiment of the fluid source management system. The first step is to perform initialization. As shown in FIG. 11C, during initialization, the lights of the visual indicator are flashed, the tubes are closed, the weights of the fluid sources (e.g., I.V. bags) are checked to determine whether they are in a normal range.

After initialization, a check bag presence subroutine can be performed. In this subroutine, the amount of fluid in the fluid sources (e.g., I.V. bags) can be checked, for example, by using the sensors 102, as shown in FIGS. 11B and 11C. As an example, values from the sensors 102 can be used to set a value to the level of fluid in each of the fluid sources to High, Low or Empty. A variable Channel_Weight (Bag) for each bag can be set to "2" for "High," "1" for "Low" and "0" for "Empty," as shown in FIG. 11C.

As shown in FIG. 11B, each fluid source is associated with a respective "Lane 1," "Lane 2," "Lane 3" and "Lane 4." A lane is defined as a path or conduit for the flow of fluid through the system including any sensor there in or interacting with or effecting the flow of fluid. A channel is a gateway for the fluid located. For example, a "High" value could be used when the amount of fluid in the fluid source is greater than approximately 80% of the capacity of the fluid source, a "Low" value could be used when the amount of fluid in the fluid source is less than approximately 20% of the capacity of the fluid source, and an "Empty" value could be used when the amount of fluid in the fluid source is less than approximately 5% of the capacity of the fluid source [QUESTION #3: PLEASE LET US KNOW IF WE SHOULD INCLUDE DIFFERENT LEVELS FOR THESE THRESHOLDS]. Various other thresholds could be used for "High," "Low," and "Empty." The indicator lights can then be set to display the fluid levels of the fluid sensors A "high" indicator signal would indicate that all fluid sources are full. A "low" indicator signal would indicate that at least one fluid source is empty and at least one fluid source contains at least 5% of maximum volume while an "empty" indicator signal would indicate that fluid levels in all fluid sources are contain less than 5% maximum volume.

As shown in FIGS. 11B and 11C, a check tube presence subroutine can be performed to detect the presence of tube sensors associated with each of the fluid sources. As shown in FIG. 11C, in this subroutine, the variable Channel_Tube (Tube) can be set to "TRUE" when a tube sensor is present and to "FALSE" when a tube sensor is not present. The indicator lights can then be set to display the status of the tube sensors When a sensor determines fluid a volume level it communicates with the controller which then selects the appropriate indicator signal for fluid levels in the fluid sources.

As shown in FIG. 11B, each Lane that satisfies the tube sensor check and has a bag value that is greater than empty is set to "In Use" and the associated Channels are set to "open". The "Cleanup set up is the logic used to determine if and when to close a lane for a empty fluid source (contains less than 5% of maximum volume of fluid) and the logic used if the fluid value is high (all fluid source contains 100% of maximum volume of fluid) or the fluid value is low (fluid source containing >5% of maximum volume and but less than maximum fluid volume) while empty is a fluid source containing <5% of maximum volume.

The bottom of FIG. 11B shows a procedure for a Cleanup Step.

As shown in FIG. 11C, after performing the check tube presence subroutine, the channels can be marked as "Available" (i.e., Channel_Available=True) if the bag for the respective channel is not empty (i.e., Channel_Weight >0) and that Channel has a tube sensor (i.e., Channel_Tube=True), and as "Not Available" otherwise. If the Channel_Available is set to True, then an LED indicator light can be set to High. If the Channel_Available is set to False, then an LED indicator light can be set to Low. The first channel that has a Channel_Available become True can be opened to supply fluid. The Channel status for this channel is set to "ON" (i.e., "Channel_Status="On"). When a channel that has a Channel_Status="on" and a Channel_Weight="1" (i.e., a "Low" level), the next available Channel can be searched for. When a channel that has a Channel_Status="on" and a Channel_Weight="0" (i.e., an "Empty" level), the Channel_Status is changed to "OFF."

FIGS. 12A-12C illustrate some aspects of an embodiment of fluid source management system 100. FIG. 12A provides a perspective view of tubing support structure 111 including central strut 106 which is connected to and runs through tubing support structure 111. Both central strut 106 and tubing support structure 111 having inner channels (not shown) through which communication wires 111E run. Communication wires 111E are connected to the system controller (not shown) through an inner channel (not shown) in central strut 106 in the direction indicated by arrow B. One of the communication wires 111E also runs through inner channel (not shown) of tubing support structure 111 and is connected to linear actuator 111D. Tubing support structure 111 has tubing acceptance bay 111A. In this embodiment tubing acceptance bay has post 111X located in the side of tubing acceptance bay 111A. In this illustration post 111X is in the fully extended position protruding from an opening (not shown) in the side of acceptance bay 111A. Post 111X is attached to linear actuator 111D which can pull post 111X in direction indicated by arrow Z into a fully retracted position whereby post 111X does not protrude from the opening (not shown) in tubing acceptance bay 111A. Linear actuator 111D can also move post 111X in the direction indicated by arrow X into a fully extended position whereby post 111X extends at its maximum length out of hole (not shown) in the side of tubing acceptance bay 111A. Acceptance bay 111A has acceptance slot 111F formed into its distal side shaped to accept plug 118 (see FIGS. 12B and 12C). Plug 118 comprises platform 118A (see FIG. 12B-C) and wings 118B (see FIGS. 12B and 12C) of adapter block 113 (see FIG. 12B-C).

FIG. 12B illustrates one embodiment of adapter block 113. Adapter block 113 has a through hole (not shown) through which tubing 104 passes into, through and out of adapter block 113. Aperture 116 is located on the side of adapter block 113 through which post 111X may pass through, thereby accessing tubing 104. Post 111X is attached to linear actuator 111D (see FIG. 12A). Adapter block 113 has wall 140 formed therein which bisects the interior of adapter block 113. Wall 140 includes a semi-circle portion 140A formed in the center of wall 140 and also bisects the adapter block 113 in the direction of arrow W-W. Semi-circle portion 140A of wall 140 can be formed so that tube 104 can fit snuggly into it. It can be seen that post 111X attached to linear actuator 111D (not shown see FIG. 12A)

of acceptance bay 111A (see FIG. 12A) can be fully extended against tubing 106 fitted into semi-circle 114 thereby compressing and completely occluding the inner lumens (not shown) of tubing 104. The linear actuator also can be partially extended pushing post 111X against tubing 106 to partially occlude the inner lumens of tubing 104.

FIG. 12C provides a top view of one embodiment of adapter block 113 of FIG. 12B (indicated by line V-V). Adapter block 113 has plug 118 with platform 118A and wings 118B formed into it shaped to fit into acceptance slot 111F (see FIG. 12A) of acceptance bay 111A of tubing support structure 111. Adapter block 113 has wall 140 formed therein which bisects the interior of adapter block 113. Semi-circle 140A is formed into the center of wall 140 so that tube 104 can fit snuggly therein. Post 111X is attached to linear actuator 111D (see FIG. 12A) of acceptance bay 111A (see FIG. 12A) and can be fully extended against tubing 106 which is fitted snuggly into semi-circle 114 thereby compressing and completely occluding the inner lumens (not shown) of tubing 104. The linear actuator 111D also can be partially extended against post 111X thereby pushing tubing 104 to partially occlude the inner lumens of tubing 104.

Figure 13A:
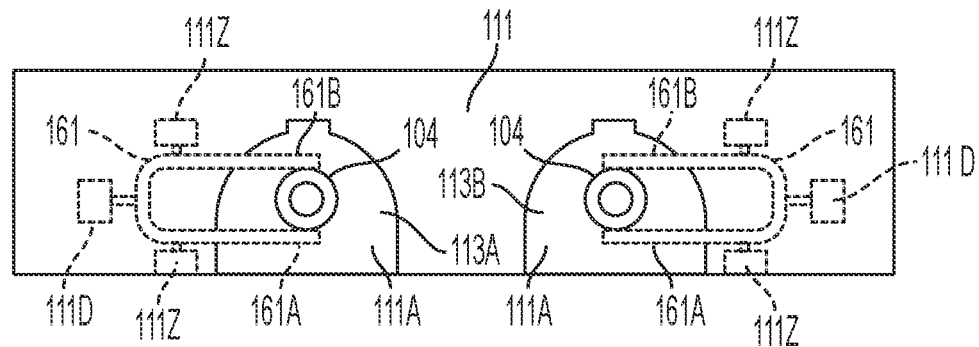
FIGS. 13A-13D illustrate another embodiment of a tubing support structure and adapter blocks.

FIGS. 13A-D show top views of one embodiment of tubing acceptance support structure 111 of fluid source management system. FIG. 13A is a top view of an embodiment of tubing support structure 111. In this view adapter block 113A and adapter block 113B are shown fitted into tubing acceptance bay 111A of tubing support structure 111. Adapter block 113A and adapter block 113B have apertures (not shown) formed into their left and right sides respectively and sized to allow scissor arms 161A and 161B of pinchers 161 to fit and egress into the interior of adapter block 113. A through hole (not shown) is formed in adapter blocks 113A and 113B allowing tubing 104 to reside in and pass through them. Scissor 161 has inner arm 161B and outer arm 161A and is attached to linear actuator 111D and linear actuators 111Z. In this view, pinchers 161 with inner scissor arm 161B and outer scissor arm 161A are shown in the fully extended position. In this fully extended position outer scissor arm 161A and inner scissor 161B extend just beyond distal edge of tubing 104. When scissor arms 161A and 161B are in the fully extended positions, scissor pads 161X (see FIG. 14A) are colinear with the outer sides of tubing 104.

Figure 13B:
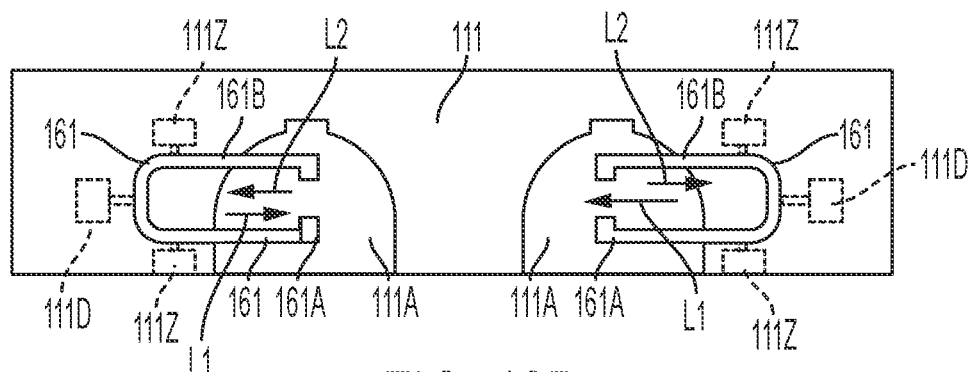

FIG. 13B provides a top view of an embodiment of tubing support structure 111 with acceptance bay 111A. Pinchers 161 with inner scissor arm 161B and outer scissor 161A is attached to linear actuator 111D which provides for actuated motion in the directions show by arrow L1 and L2. Linear actuator 111D can fully extend pinchers 161 out of hole (not shown) in the side of acceptance bay 111A. Pinchers 161 with inner arm 161B and outer arm 161A are shown in the fully extended position in FIG. 13B. Pinchers 161 are also attached to linear actuators 111Z.

Figure 13C:
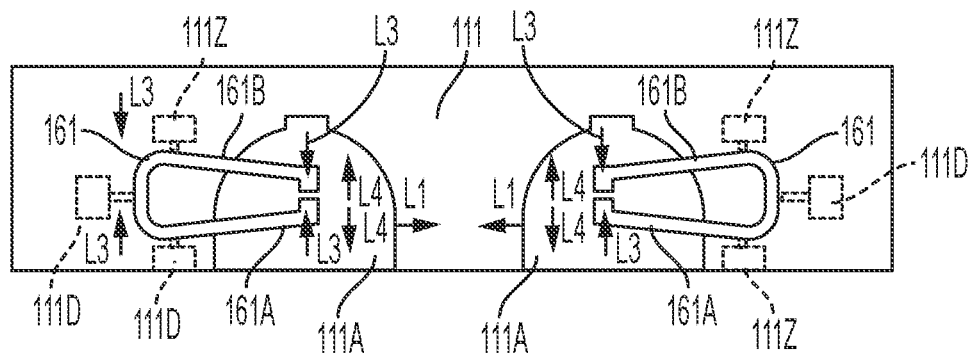

FIG. 13C provides a top view of an embodiment of tubing support structure 111 with acceptance bay 111A. Pinchers 161 with inner arm 161B and outer arm 161A are attached to linear actuator 111D and linear actuators 111Z. In this view pinchers 161 are shown in the fully extended position extending outwardly from hole (not shown) in the side of acceptance bay 111A. Linear actuator 111D provides for linear motion of inner scissor arm 161B and outer scissor arm 161A in the direction of L3 (towards each other) and L4 (away from each other). In this view, inner scissor arm 161B and outer scissor arm 161A are in the fully closed position due to the action of linear actuator 111Z in the arrow L3 direction.

Figure 13D:
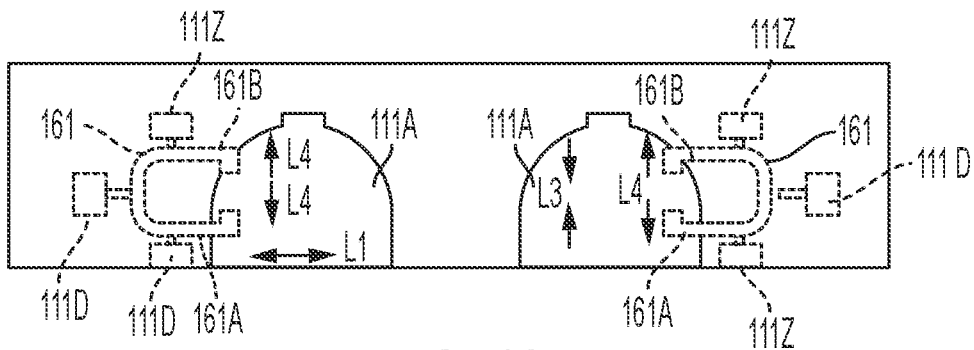

FIG. 13D provides a top view of an embodiment of tubing support structure 111 with acceptance bay 111A. Pinchers 161 with inner arm 161B and outer arm 161A are attached to linear actuator 111D and linear actuators 111Z. Linear actuator 111D provides motion in the direction shown by arrow L1. In this view, pinchers 161 are shown in the fully retracted position inside tubing support structure 111. Linear actuators 111Z provide for linear motion of inner scissor arm 161B and outer scissor arm 161A in the direction of L3 (towards each other) and L4 (away from each other). In this view inner scissor arm 161B and outer scissor arm 161A are in the fully open position as also shown in FIG. 13A.

Figure 14A:
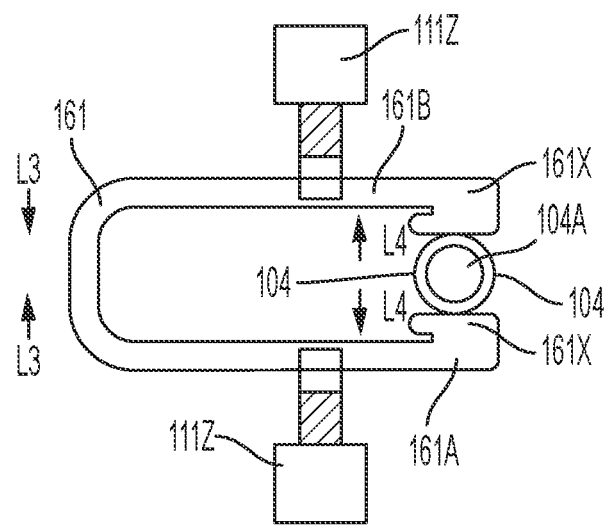
FIGS. 14A and 14B illustrate the pinchers and linear actuator of the embodiment shown in FIGS. 13A-13D.
Figure 14B:
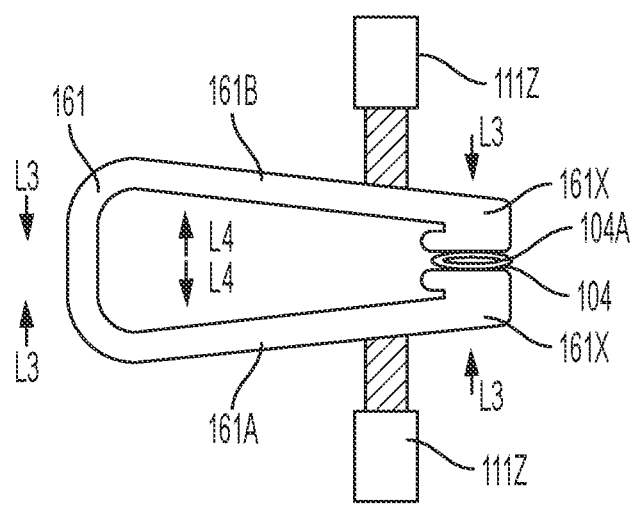

FIGS. 14A-B provide a top view and details of pinchers 161 and linear actuators 111Z of FIGS. 13A-D. FIG. 14A provides a view of Pinchers 161 with inner scissor arm 161B and outer scissor arm 161A. Scissor arms 161A and 161 B have pads 161X formed into their ends. Scissor arms 161A and 161B are attached to linear actuators 111Z. Linear actuators 111Z provide linear motion in directions shown by arrows L3 and L4 for scissor arms 161A and 161B. In this view, scissor arms 161A and 161B are in the fully open position with pads 161X colinear with the outer edges of tubing 104 with inner lumens 104A. FIG. 14B provides a top view of pinchers 161 with scissor arms 161A and 161B attached to linear actuators 111Z. Linear actuators 111lZ provide linear motion in directions shown by arrows L3 and L4 for scissor arms 161A and 161B. In this view, linear actuators 111Z have provided maximum motion for scissor arms 161A and 161B in the direction of arrow L3 putting pinchers 161 in the closed position and allowing pads 161X to compress tubing 104 thereby occluding inner lumen 104A.

Those having ordinary skill in the art will appreciate that various changes can be made to the above embodiments without departing from the scope of the invention.

The above detailed description refers to the accompanying drawings. The same or similar reference numbers may have been used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

The foregoing description of the embodiments has been presented for purposes of illustration only. It is not exhaustive and does not limit the embodiments to the precise form disclosed. While several exemplary embodiments and features are described, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. As used herein, the singular forms "a," "an," and "the" may include the plural forms unless the context clearly dictates otherwise. Further, the term "coupled" does not exclude the presence of intermediate elements between the coupled items. Also, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system. Further, unless stated otherwise or deducted otherwise from the context, the conjunction "or," if used, is not exclusive, but is instead inclusive to mean and/or. Moreover, if these terms are used, a subset of a set may include one or more than one, including all, members of the set.

Further, if used in this disclosure, and unless stated or deducted otherwise, a first variable is an increasing function of a second variable if the first variable does not decrease and instead generally increases when the second variable increases. On the other hand, a first variable is a decreasing function of a second variable if the first variable does not increase and instead generally decreases when the second variable increases. In some embodiment, a first variable may be an increasing or a decreasing function of a second variable if, respectively, the first variable is directly or inversely proportional to the second variable.

The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents. Further, the present disclosure is directed toward all novel and non-obvious features and aspects of the various disclosed embodiments, alone and in various combinations and sub-combinations with one another.

While the present disclosure has been particularly described in conjunction with specific embodiments, many alternatives, modifications, and variations will be apparent in light of the foregoing description. It is therefore contemplated that the appended claims will embrace any such alternatives, modifications, and variations as falling within the true spirit and scope of the present disclosure.

What is claimed is:

1. A fluid source management system comprising:
a structure that supports one or more fluid sources for storing a fluid;
sensors that determine a fluid state of the one or more fluid sources;
at least one common reservoir for storing the fluid;
tubing connecting the fluid sources to the at least one common fluid reservoir; affectors located between the fluid sources and the at least one common reservoir that open and close thereby allowing and preventing fluid flow through the tubing;
a connector manifold configured to be attached to, or formed in, the at least one common reservoir, the connector manifold forming a fluid connection between the tubing and the at least one common reservoir;
a controller that controls opening and closing of the affectors based upon the fluid state of the fluid sources; and
a tubing support structure having at least two tubing acceptance bays formed therein, wherein the connector manifold comprises at least two protuberances that are configured to be removably fit into a corresponding one of the at least two tubing acceptance bays, wherein apertures are formed in the protuberances that allow a corresponding one of the affectors to move therethrough thereby opening and closing internal tubing formed in the protuberances.

2. The fluid source management system of claim 1, wherein the tubing support structure comprises a shelf formed in the bottom thereof that is configured to hold the common reservoir.

3. The fluid source management system of claim 1, wherein the common reservoir comprises a structure that prevents the common reservoir from collapsing.

4. The fluid source management system of claim 3, wherein the structure comprises a three-dimensional polygon.

5. The fluid source management system of claim 1, wherein the controller is configured to maintain at least one affector in an open state and maintain remaining affectors in a closed state.

6. The fluid source management system of claim 1, wherein the controller is configured to maintain at least one affector in a first open state and maintain remaining affector in a closed second state.

7. The fluid source management system of claim 1, wherein the controller is configured to maintain at least one affector in an open state and maintain remaining affectors in an open or closed state.

8. A fluid source management system comprising:
a structure that supports one or more fluid sources for storing a fluid;
sensors that determine a fluid state of the one or more fluid sources;
at least one common reservoir for storing the fluid;
tubing connecting the fluid sources to the at least one common fluid reservoir;
a controller that controls opening and closing of the tubing based upon the fluid state of the fluid sources, wherein the controller is configured to control opening and closing of affectors that open and close the tubing so as to maintain an amount of fluid in the at least one common reservoir;
affectors located between the fluid sources and the at least one common reservoir that open and close the tubing thereby allowing and preventing fluid flow through the tubing to at least one the common reservoir; and
adapter blocks that encapsulate the tubing; and a tubing support structure having tubing acceptance bays formed therein that are configured to removably receive the adapter blocks, wherein the affectors are positioned in the tubing support structure such that the affectors can extend into a corresponding tubing acceptance bay and adapter block thereby interacting with the tubing to open and close the tubing, wherein the affectors comprise posts that extend through apertures formed in the acceptance bays, and the fluid source management system further comprises linear actuators that move a corresponding post between a retracted position in which the post does not protrude into a corresponding tubing acceptance bay and an extended position in which the post extends into a corresponding tubing acceptance bay so as to occlude the tubing and prevent the fluid from passing through the tubing.

9. A fluid source management system comprising:
a structure that supports one or more fluid sources for storing a fluid;
sensors that determine a fluid state of the one or more fluid sources;
at least one common reservoir for storing the fluid;
tubing connecting the fluid sources to the at least one common fluid reservoir;
a controller that controls opening and closing of the tubing based upon the fluid state of the fluid sources, wherein the controller is configured to control opening and closing of affectors that open and close the tubing so as to maintain an amount of fluid in the at least one common reservoir;
affectors located between the fluid sources and the at least one common reservoir that open and close the tubing thereby allowing and preventing fluid flow through the tubing to the at least one common reservoir; and
adapter blocks that encapsulate the tubing; and a tubing support structure having tubing acceptance bays formed therein that are configured to removably receive the adapter blocks, wherein the affectors are positioned in the tubing support structure such that the affectors can extend into a corresponding tubing acceptance bay and adapter block thereby interacting with the tubing to open and close the tubing, wherein the affectors comprise scissor arms that extend through the adapter blocks, and the fluid source management system further comprises linear actuators that move the scissor arms between a retracted position in which the scissor arms do not protrude into a corresponding tubing acceptance bay and an extended position in which the scissor arms extend into a corresponding tubing acceptance bay beyond a distal edge of the tubing, and linear actuators that move the scissor arms between an open position in which the scissor arms do not compress the tubing and a closed position in which the scissor arms compress the tubing so as to occlude the tubing and prevent the fluid from passing through the tubing.

10. The fluid source management system of claim 4, wherein the structure is made of foam.

\* \* \* \* \*